United States Patent
Lewis

(10) Patent No.: US 12,232,934 B2
(45) Date of Patent: Feb. 25, 2025

(54) MEDICAL DRESSINGS AND USES THEREOF

(71) Applicant: Marine Biology & Environmental Technologies, LLC, Tarzana, CA (US)

(72) Inventor: Eric Lewis, Tarzana, CA (US)

(73) Assignee: Marine Biology & ENvironmental Technologies, LLC, Tarzana (CA)

( * ) Notice: Subject to any disclaimer, the term of this patent is extended or adjusted under 35 U.S.C. 154(b) by 199 days.

(21) Appl. No.: 17/037,669

(22) Filed: Sep. 30, 2020

(65) Prior Publication Data

US 2021/0007899 A1 Jan. 14, 2021

Related U.S. Application Data

(63) Continuation-in-part of application No. PCT/US2019/025343, filed on Apr. 2, 2019.
(Continued)

(51) Int. Cl.
*A61F 13/00* (2024.01)
*A61F 13/02* (2024.01)
(Continued)

(52) U.S. Cl.
CPC .... *A61F 13/0203* (2013.01); *A61F 13/00063* (2013.01); *A61F 13/0259* (2013.01);
(Continued)

(58) Field of Classification Search
CPC .......... A61F 13/00017; A61F 13/00038; A61F 13/025; A61F 2013/00604; A61F 2013/00412; A61F 2013/00902; A61F 2013/00863; A61F 2013/00582; A61F 2013/00685; A61F 2013/00817; A61F 2013/00719; A61F 2013/00089;
(Continued)

(56) References Cited

U.S. PATENT DOCUMENTS 3,367,329 A 2/1968 Dibelius
3,426,754 A 2/1969 Bierenbaum et al.
(Continued)

FOREIGN PATENT DOCUMENTS

CN 102223858 A * 10/2011 ....... A61F 13/00008
EP 0107051 A2 * 5/1984
(Continued)

*Primary Examiner* — Ophelia A Hawthorne
*Assistant Examiner* — Michael Milo
(74) *Attorney, Agent, or Firm* — The Fedde Law Firm; Kenton Fedde; Nathaniel Fedde

(57) ABSTRACT

This invention provides compositions and methods of treating subjects with wounds. Compositions include dressings comprising a sheet and an adhesive, wherein the adhesive is adhered to the sheet, and wherein the sheet has channels. In some embodiments, the channels comprise two different classes of channels (e.g. liquid channels and air channels). These dressing can be applied to various kinds of skin injuries and remain affixed, protecting the injury from contaminants and at the same time, allowing exchange of exudates on the proximal (injury) side to the distal side and exchange of topical agents applied from the distal side of the dressing to the wound while also allowing exchange of gasses from the injury to the air and air to the wound.

16 Claims, 13 Drawing Sheets

Related U.S. Application Data

(60) Provisional application No. 62/651,711, filed on Apr. 2, 2018, provisional application No. 62/908,599, filed on Oct. 1, 2019.

(51) Int. Cl.
*A61F 13/0203* (2024.01)
*A61L 15/28* (2006.01)
*A61L 15/58* (2006.01)

(52) U.S. Cl.
CPC ............... *A61L 15/28* (2013.01); *A61L 15/58* (2013.01); *A61F 2013/00157* (2013.01)

(58) Field of Classification Search
CPC . A61F 2013/00361; A61M 2025/0206; A61M 2025/01213; A61M 2025/0246; A61M 2025/0253; A61M 2025/0266; A61M 25/02; A61B 46/23
USPC ................................. 602/47, 56, 57; 604/180
See application file for complete search history.

(56) References Cited

U.S. PATENT DOCUMENTS

| | | | |
|---|---|---|---|
| 4,499,896 A * | 2/1985 | Heinecke | A61F 13/00063 602/57 |
| 4,944,958 A * | 7/1990 | Langen | A61L 15/58 523/111 |
| 5,010,883 A * | 4/1991 | Rawlings | A61F 13/023 428/305.5 |
| 5,244,457 A | 9/1993 | Karami et al. | |
| 5,571,080 A * | 11/1996 | Jensen | A61L 15/58 602/56 |
| 5,810,756 A | 9/1998 | Montecalvo et al. | |
| 6,794,554 B2 * | 9/2004 | Sessions | A61F 13/01021 604/290 |
| 2003/0032980 A1* | 2/2003 | Stenton | A61B 17/00491 606/213 |
| 2007/0026056 A1* | 2/2007 | Rolf | A61F 13/023 424/769 |
| 2007/0068837 A1 | 3/2007 | D'angelis | |
| 2007/0212520 A1* | 9/2007 | Furumori | A61F 13/0269 428/137 |
| 2008/0095979 A1 | 4/2008 | Hatanaka et al. | |
| 2011/0195625 A1* | 8/2011 | Keener | B32B 25/10 442/151 |
| 2012/0308637 A1 | 12/2012 | Chamberland et al. | |

FOREIGN PATENT DOCUMENTS

| | | | | |
|---|---|---|---|---|
| JP | 3027002 B2 * | 3/2000 | ........... | A61F 13/023 |
| WO | WO-9725012 A1 * | 7/1997 | ........... | A61F 13/023 |
| WO | WO-9939756 A2 * | 8/1999 | ......... | A61F 13/0223 |

* cited by examiner

MEDICAL DRESSINGS AND USES THEREOF

TECHNICAL FIELD

The instant invention relates to medical bandages or dressings of the type employed in the direct application thereof to an area of injury and improved methods of injury repair.

BACKGROUND

Wound healing is a complex process that requires a highly regulated series of events including inflammation, tissue formation, revascularization and tissue remodeling. However, this is impaired in certain pathological conditions such as thrombosis, ischemia, diabetes and infection.

The art of medical dressing or bandage construction is ancient and a tremendous variety of such materials are available on today's commercial market. Among these various dressings or bandages now available, there may be mentioned surgical dressings, first-aid type bandages, such as Band-Aids®, military medical bandages, operational bandages, such as swabs, and the like. In general, these prior art bandages comprise a layer of absorbent material, such as gauze, which is applied to the injured area of the skin by means of an adhesive material associated therewith which is applied to an adjacent uninjured area. In use, a medicament is usually initially applied to the injury to aid the healing process and the bandage or dressing is then applied thereover.

Dressings can be applied to large area wounds, whether massive abrasions or burns or deep open wounds, in order to protect the wound surface, absorb fluids exuded from the wound and to let air into the surface of the wound. It is important to prevent the contamination of the wound without impeding the progress of the natural healing process of the body, and in some cases, to protect the environment against contamination from the wound.

Body fluids tend to exude from an open wound or massive burn area. Absorbent materials such as gauze are often applied to the wound surface in order to remove such fluids, permitting it to dry; this furthers the healing process. It is also necessary at the same time to control the loss of fluid. It is most advantageous, especially when dealing with massive burns, to insure against shock by preventing the excessive loss of the salts from the body which generally are dissolved an any body fluids which may be exuded. Therefore, by limiting the loss of body fluids, the loss of salts is also impeded, thereby decreasing the chances of severe shock.

Previous attempts have been made to prepare bandages which are impermeable to the passage of liquids, but selectively permeable to specific gases and vapors. In U.S. Pat. No. 3,367,329, (Dibelius), there is described a surgical bandage including a nonporous membrane, impermeable to liquids and infectious organisms but selectively permeable to specific gases and vapors. In other words, the material is a membranous material that permits the diffusion of vapors, which diffusion is due to the partial pressure differential and is not related to the conventional filtering process). Such a material is insufficiently permeable compared to the usual porous bandage material, and thus fails to provide the necessary transpiration from the wound surface. Further, there is no provision for absorption of any body fluids exuded from a wound or burn area. The Dibelius membrane is indicated as being a thin, permeable silicone rubber membrane having the desired permeability.

U.S. Pat. No. 3,426,754 (Bierenbaum et al.) describes a medical dressing comprising a film having a pressure-sensitive adhesive applied thereto. The film is described as a porous material having an open-celled structure permeable to gases. The void or pore sizes of the open cell structure accessible to the exterior of the film is described as being under 5,000 angstrom units, e.g., 100 to 500 angstrom units. The film of Bierenbaum et al. is prepared from a group of relatively crystalline film-forming polymers having a defined elasticity. These films are prepared by a special process which forms the open cell structure in the film. The film can be formed from various hydrocarbon polymers, acetal polymers or a miscellaneous group of polymers including polyalkylene sulfides, polyphenylene oxides, polyamides polyesters. Films of this type are also relatively inefficient and fail to provide the necessary amounts of air and moisture vapor to and from the wound surface; they have a low dirt capacity, so that the amount of air which can be passed in quickly decreases once the film is exposed to even a slightly dusty environment. Bierenbaum et al. further disclose the use of the porous film in combination with a pad or facing, covered by a wrapping or cover which functions to hold the facing in position.

Another problem common to most adhesive tapes and bandages is that they prevent air from reaching the area which they cover, thus impeding the healing processes of the body. When the usual adhesive tapes and dressings are applied over draining wounds, they restrict the flow of fluid and aggravate the damaged area. If these prior art tapes are placed to the side of the wound, the wound covering soon slips from place.

Still another disadvantage with the prior art adhesive tapes and dressings is that they are painful to remove, especially where they are in contact with hair-covered skin. The least painful way of removing these adhesives is to jerk them off with a quick pull away from the skin, but even this method causes discomfort, particularly where a large area is involved.

Another problem with bandages of the art is that they can be absorbent and capable of retaining, after absorbing, the body fluids exuded from the wound, preventing the passage of the exuded liquid outside of the bandage.

There remains a long felt need for a dressing which allows the free exchange of vapor, moisture, fluids, and air bi-directionally through the dressing, that is capable of remain affixed for days and weeks, is easily removable, and provides protection from physical and microbial assault.

SUMMARY OF THE INVENTION

This instant invention provides a dressing comprising a sheet and an adhesive,
  a) wherein the adhesive is adhered to the sheet,
  b) wherein the sheet has channels,
  c) wherein the channels density is 1 to 16,000, and
  d) wherein the diameter of the channels are 25 μm to about 10 mm.

In one embodiment, the sheet comprises sheet material that is air and liquid permeable.

In one embodiment, the dressing comprises a plurality of channels of a first channel type and a plurality of channels of a second channel type, wherein the first and second channel types differ by diameter, shape, or configuration and optionally wherein the sheet is a plant product or animal product or combination thereof.

Optionally, the first channel type is an air channel having a diameter of about 25 μm to about 2500 μm and facilitates exchange of air and gases between the proximal (wound) side and the distal side of the sheet and the second channel type is a liquid channel having a diameter of about 250 µm to about 10 mm and facilitates exchange of exudates, water, vapor, moisture, and liquid from the proximal side to the distal side and topical agents, moisturizers, and emollients between the distal side and the proximal side.

Optionally, the instant invention further comprises a protective layer releasably secured on the proximal side (side comprising adhesive) or distal side. Optionally, the instant invention further comprises a first protective material releasably secured on the proximal side of the dressing and a second protective material releasably secured on the distal side of the dressing.

BRIEF DESCRIPTION OF THE DRAWINGS

FIG. 1A shows three embodiments of the invention, each having air channels and liquid channels.

DETAILED DESCRIPTION OF THE INVENTION

Figures 1, 1B:
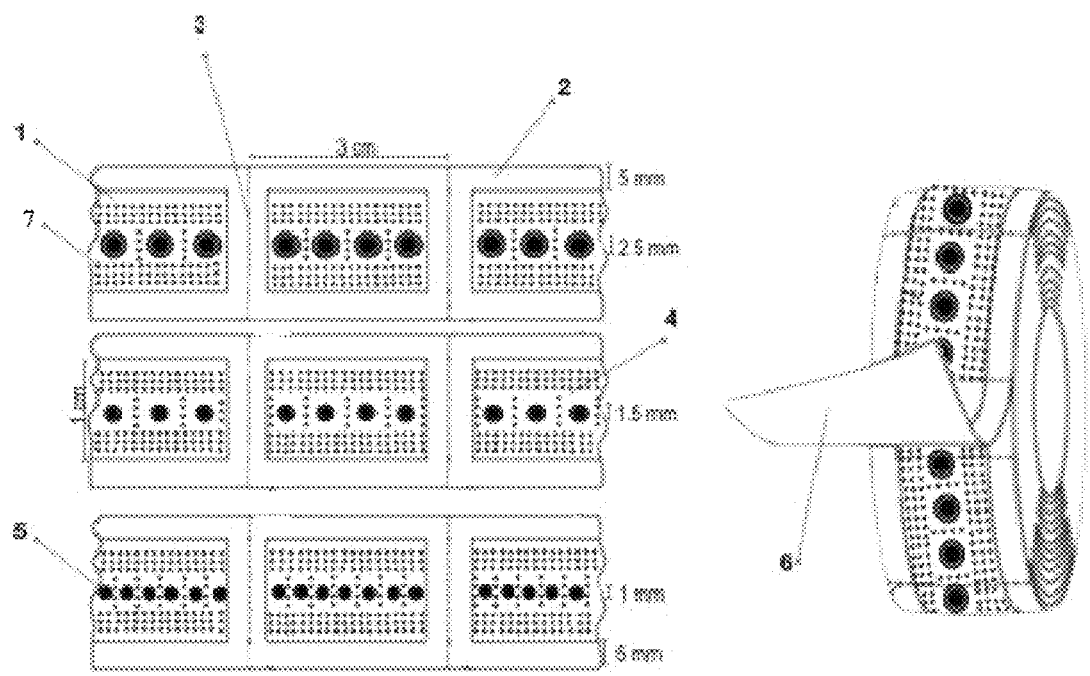
FIG. 1B shows a roll comprising one of the embodiment shown in FIG. 1A.

As used here, the following definitions and abbreviations apply.

"Antimicrobial" refers to agents that kill microorganisms or inhibits their growth. Antimicrobials include antibiotics, disinfectants, and antiseptics.

"Channels density is the number of channels per $cm^2$ of sheet. Optionally, in embodiments with non-perforation zones, channel density can be expressed as the number of channels per $cm^2$ of the channel zone.

"Channel diameter", as used here, refers to the diameter measure at the distal surface of the sheet.

"Channel zone" refers to instant embodiments that comprise a non-perforation zone wherein the channel zone is the region of the sheet that contains channels.

"Distal side: of the dressing refers to the side opposite the proximal (or wound) side. A distal side can be configured, e.g., without an adhesive applied thereto.

"Dressing" as used here means any of a bandage, pad, compress, and medical tape. In certain preferred embodiments, "dressings" are to be distinguished from sticking plaster or adhesive bandage.

"Elastic" as used here means the property of the instant invention which, upon application of a biasing force, is stretchable, that is, elongatable, at least about 10 percent (i.e., to a stretched, biased length which is at least about 110 percent of its relaxed unbiased length), and which, will recover at least 55 percent of its elongation upon release of the stretching, elongating force. It has been discovered that an especially suitable material for the instant sheet is capable of elongation from about 20% to about 30%.

"Exemplary" (or "e.g." or "by example") means a non-limiting example.

"Exchange functions", as used here, refer to the function of the instant dressing to facilitate air permeability, water permeability, vapor permeability, and/or wicking.

"Excipients" means any material that is combined with a drug in order to produce a drug dosage form. Such excipients can be combined in order to produce a desired skin feel or to facilitate drug delivery. Non-limiting examples of excipients include, for example, water, thickeners, humectants, keratolytics, oils, emollients, surfactants, preservatives, colorants, UV blockers (e.g. UVA and UVB), antioxidants, perfumes, mineral oil, liquid petrolatum, and white petrolatum. An excipient may also serve a solvent function. For example, polysorbate and panthenol have properties as a humectant and as a solvent.

"Instant", in reference to the invention, sheet, adhesive, embodiments, and the like, mean this invention, sheet, adhesive etc. as taught herein.

"Natural biologic agent", as used here, is an agent comprising a botanical extract, a plant extract, an animal extract, or combinations thereof. "Extract" is intended to embrace a solvent extract or agents that are purified therefrom.

"Natural marine extract" as used here, is a topical agent comprising extracts from marine animals or marine plants or combinations thereof.

"Non-perforation zone" refers to an area of the sheet (e.g. at the periphery) that does not contain channels.

"Proximal side" of the dressing refers to the side contacting the wound. The proximal side of a sheet used in the present invention includes an adhesive adhered thereto.

"Rayon" means a material manufactured from a fiber made from regenerated cellulose fiber. Examples of rayon are viscose, modal, and lyocell.

"Sheet" as used here, means any 3 dimensional shape having a width, a length, and a thickness where the thickness is a small fraction of the width or length. By way of none-limiting example, the thickness can be less than $1/5^{th}$ of the width or length, or less than $1/20^{th}$, $1/100^{th}$, or $1/1000^{th}$, or $1/10,000^{th}$ of the width or length.

"Star shape" means a star polyhedron, an isotoxal polygon, or a uniform polyhedron. With respect to "star-shaped channels", the star shape is formed at the aperture of the channel at the proximal or distal side (or at a cross-section of the channel where the sectioning is co-planar with the sheet).

"Topical agent" means a bioactive agent, when topically applied, can have a therapeutic effect. "Agent" is not intended to be restricted to a single component.

"Topically" refers to application of the compositions of the instant technology to the surface of the skin or broken skin (e.g. a wound) and mucosal cells and tissues.

"Treatment" (or "treat") refers to preventative or therapeutic action for a condition with clinically relevant symptoms. The use of "treatment" contemplates conditions of a wound that make the subject susceptible to microbial infection. A treatment is successful if microbial infection is prevented in a subject at risk, or if the clinical course of a microbial infection is altered (e.g. slowed progression or accelerated regression). A treatment is also deemed successful if the healing is accelerated when compared to substantially the same wound without application of the instant invention.

"Wound" refers broadly to injuries to tissue including the skin, subcutaneous tissue, muscle, ligaments, nerves, blood vessels, bone, and other structures initiated in different ways, for example, surgery, (e.g., open post-cancer resection wounds, e.g. removal of melanoma and breast cancer, etc.), contained post-operative surgical wounds, pressure sores (e.g., from extended bed rest), wounds induced by trauma, puncture wounds, scrapes, cuts, and burns. The term is not limiting with respect to the cause, e.g., a physical cause such as bodily positioning (e.g., as in bed sores) or an impact as with trauma, surgical process a chemical process such as a burn or exposure to a caustic chemical substance, or a biological cause such as a disease process, an aging process, an obstetric process, or any other manner of biological process.

It is an object of the instant invention to provide a surgical dressing which provides superior attributes including the ability to transfer body fluids exuded from the wound, to protect the wound surface, and to permit the transpiration of air, topical agents, water, and moisture between the atmosphere and the wound surface.

It is a further object of the instant invention to provide a surgical dressing which also reduces the passage of microorganisms to or from the wound surface while retaining the ability to permit transpiration of air and moisture during use.

It is a further object of the instant invention to provide a surgical dressing that can remain on a wound without the need for frequent (e.g. daily) or periodic removal and replacement, e.g., while providing superior exchange functions during the entirety of said non-removal period.

Hypoallergenic

Optionally, the instant dressings are hypoallergenic, meaning that they are free of compounds generally recognized as causing a negative dermal response such as contact dermatitis, inflammation, or other skin reactions. For example, some embodiment are substantially free of latex. Other embodiments are substantially free of Mastisol (e.g. in the adhesive).

The instant adhesives are optionally substantially free of hydroabietic acid (an industrial derivative of colophony); a glycerol ester of hydrogenated abietic acid (e.g. as a wood rosin derivative used as an adhesive); tricresyl phosphate (e.g. a plasticizer in a vinyl backing); 2,5-di(tertiary-amyl) hydroquinone (e.g., as an antioxidant in an adhesive); benzoyl peroxide (e.g. used to increase the stretch potential of some adhesive tapes); epoxy resin (e,g. used to promote adhesion in an adhesive); dodecyl maleamic acid and octadecyl maleamic acid (adhesives); diethyldithiocarbamate (e.g. as a preservative in an adhesive); tetrahydrofurfuryl acrylate (e,g, as an adhesive);[1] and p-tertbutylphenol formaldehyde resin (e.g. an acrylate polymer used as a contact adhesive owing to its flexibility, strength, and rapid onset of action).

The instant dressings are optionally substantially free of chemicals or products in Table 1

TABLE 1

| Allergenic Compounds and Products | |
|---|---|
| Tetrahyrdrofurfuryl rnethacrylate | Trimethylol propane triglycidyl ether |
| Zinc ethylenebis (dithiocarbamate) | Trirnethylol propane triacrylate |
| Isooctyl acrylate | 2-Phenylidone |
| Mastisol Liquid Adhesive | Cyclohexanone resin |
| Dirnethylphthalate | Triglycidyl isocyanurate |
| Compound benzoin tincture | Isoophorone diisocyantate |
| Octadecyl rnaleamic acid | Triethylene glycol dimethacryrlate |
| N,n-dirnethyl•p-toluidine | Ethyl alpha-cyanoacrylate |
| Triethylenetetriamine | Hydroxypropyl acrylate |
| Diethylenetriamine | 2-Hyrdroxy propyl methacrylate |
| Isophorone diamine | I,6-Hexanediol diacryrlate |
| Hexamethyrlenetetramine | Tetraethylene glycol dimethacrylate |
| Bisphenol A | Butyrl acrylate |
| Dioctyl phthalate | 2-Ethylhexyl acrylate |
| 2(2-Hydroxy-5•rnethylphenyl) benzotriazol | Triethylene glycol dimethacrylate |
| Benzoyl peroxide | 4•tert•Butylcatechol (PTBC) |
| Dibutyl phthalate | Colophony |
| Tricresyl phosphate | p-Phenylenediarnine |
| Triphenyl phosphate | Epoxy resin (bis•A) |
| Resorcinol rnonobenzoate | p-tert-Butylphenol formaldehyde resin |
| Hyrdroquinone | 2,6-di-tert-Butyl-4-cresol |
| Abitol | 2-tert-Butyl-4-cresol |
| 4-tert•Butylphenol | Phenol formaldehyde resin |
| Diphenyl thiourea | Ethyleneglycol dimethacrylate |
| Toluene-2,4-diisocyanate | 2-Hyrdroxyethyl methacrylate |
| Diphenylrnethane-4,4-diisocyanate | Methyl methacrylate |
| N,n'-dimethy thiourea | Ethyl acrylate |
| Ethylbutyl thiourea | Mercaptobenzothiazole |
| Niax | Carba mix |
| Dibutyl thiourea | Thiuram mix |
| Resorcinol | Tegaderm (3M) |
| Methylene•bis•thiocyanate | MicroporeTM 1530 (3M) |
| Diethyl thiourea | Steri•Strip Blend Tone Skin Closures (3M) |
| Ethyl methacrylate | Transpore Surgical Tape (3M) |
| n•Butyl methacrylate | Meditrace Pre-gelled Cardiac Snap Electrodes (Kendall) |
| 3-Methyl•thiazolidone-thione-2 | Curity Plastic Bandages-Latex Free (Kendall) |
| Dodeqcylrnercaptan | NexcareTM Sheer Bandages (3M) |
| Bisphenol F epoxy resin | Adhesive Bandage-Sheer (Curad) |
| 1,6-Hexamethylene diisocyanate | Band-Aid Brand-Sheer Comfort Flex (Johnson & Johnson)) |

Sheet

Sheet Material

The sheets of the instant invention can be made of any suitable material.

For example, the sheet can be made from an animal product(s), a plant product(s), a synthetic (man-made) product(s), or a combination thereof.

Examples of suitable animal-derived sheets are sheets made from silk, hair or fur. Examples of animals from which suitable fibers are made are alpaca, angora, byssus, camel, dog, guanacom, llama, angora goat, musckox, rabbit, insects, vicuña yak Examples of suitable plant-derived sheets are sheets made from abaca, sugarcane, sorghum, bamboo, coconut, cotton, flax, hemp, plants of the genus Corchorus, jute, *Ceiba pentandra*, kenaf, pineapple, pine, raffia palm, ramie, rattan sisal wood Examples of suitable plant-derived sheets are bagasse, coir, cotton, fique, linen, hemp, jute, kapok, piña, vegetable flannel, and paper.

Examples of suitable synthetic sheets are those made of acrylic, aramid, twaron, Kevlar, technora, nomex, microfiber, modacrylic, nylon, olefin, polyester, polyethylene, dyneema, spectra, spandex, vinylon, vinyon, zylon.

Optionally, the sheet can be made from a fibrous material (e.g. woven or non-woven fibrous material). Alternatively, the sheet can be made from a non-fibrous material (e.g. non-fibrous molded article).

Optionally, the sheet can be made from a woven or non-woven product.

Optionally, the plant-based sheet can be a cellulosic sheet.

Optionally, the cellulosic sheet can be rayon.

Optionally, the cellulosic sheet can be paper.

Optionally, the cellulosic sheet can further comprise fillers such as chalk or china clay to further modify its characteristics.

Optionally, the sheet is made of a synthetic product which can be a thermoplastic product.

Optionally, the sheet can incorporate metal-based antimicrobial substances such as, for example, those disclosed in U.S. Pat. No. 5,662,913, U.S. Patent Application Publication No. US 2012/0089068, US20070292469, US20100203028, and US20140308867, US20070292469.

Sheet Elasticity

While the sheet of some embodiments of the instant invention is non-elastic, other embodiments possess sheet elasticity. For example, some embodiments are able to elongate 10% or more before the sheet material breaks or fractures and recover at least 55 percent of its elongation). In other embodiments, the dressing can elongate 20% or more or 50% or more. The skilled artisan, with the teaching herein, will readily appreciate that dressings with these properties can be readily produced by varying the selection of the sheet material, thickness, optionally the weave and inclusion of other fibers.

When an elastic dressing is stretched before applying, the dressing is able to provide lateral forces on the skin (for example, to hold a wound together or to stop bleeding).

In one embodiment, an elastic dressing is manufactured by joining a nonelastic sheet material to an elastic sheet material while the elastic sheet material is in a stretched condition so that when the sheet material is relaxed, the nonelastic material gathers between the locations where it is bonded to the elastic fabric. The resulting composite elastic sheet is stretchable to the extent that the nonelastic material gathered between the bond locations allows the elastic sheet to elongate. An example of this type of composite material is disclosed, for example, by U.S. Pat. No. 4,720,415 to Vander Wielen et al., issued Jan. 19, 1988.

Optionally, the sheet is of a thickness sufficient to provide sufficient wear resistance to maintain its usefulness over a period of time such as days or tens of days.

The material scientist, with the teaching herein, will readily appreciate how to use the various plant products, animal products, or synthetic products (or combinations thereof) to manufacture sheets with the required properties.

Dimensions

The inventor has discovered the unexpected benefit of providing a dressing that is available in any and various sizes. The instant invention can optionally be on a roll, e.g. as shown in FIG. 1b. Typical sizes are 4 mm-50 cm wide and any length, e.g. 100 mm to 20 meters (e.g. on a roll).

Optionally, the instant dressings are divided into segments separated by linear perforations (see perforations 3, FIG. 1a) that facilitate linear tearing or separation into a plurality of pieces. This allow the subject who is applying the dressing to size or custom fit the dressing to a size more suitable for a particular wound without the use of scissors.

By way of example, the dressings shown in FIG. 1A have sheets with a width of 1 cm and a protective layer that extends 5 mm on each side that defines the width; the lengths of each segment is 3 cm. The protective layer extends 5 mm on each side that defines the length.

Functional Properties

The instant sheets provide bilateral exchange of gases, vapor, and liquid while at the same time, providing substantial protection from air-born contaminants such as infectious agents, irritants, and particulate matter.

In some embodiments, the thickness of the sheet can also provide protection from physical insult that can result from interaction with objects such as clothing, bedding, and accidental encounters.

As discussed herein, the functional properties of the sheet are sometimes referred with respect to the dressing. However, it is to be understood that these functional properties are referenced with respect to the dressing once any protective layer (if present) is removed.

Sheet Permeability

Air permeability, water permeability, vapor permeability, and wicking (i.e. exchange functions) are each important functional characteristics of the dressing of the instant invention. Structural features that contribute to these characteristics are the channels and optionally the sheet material. With respect to the sheet material, exchange functions are influenced by the type of sheet material and the material structure. For textile fabric sheets (i.e. flexible material consisting of a network of natural or artificial fibers), the material can be at diverse densities or weaves. For woven fabric, the design of the weave, the number of warp and weft yarns per centimeter, twist, size of fibers, and the fiber structure, presence of fabric treatments, etc., can each effect exchange functions.

With respect to exchange functions of the channels, these are established by the density, size, shape, and orientation of the channels.

Permeability: Testing of Exchange Functions

The properties of the instant invention can be demonstrated by any method known to the skilled artisan. The following are examples of useful methodology to demonstrate superior properties of the instant invention. While the exchange functions result from the combined interaction of the sheet material, the channels, and the adhesive, such functions can also be tested on the dressing or on the sheet without channels or adhesive.

Air Permeability

Air permeability can be measured as the rate of air flow passing perpendicularly through a known area of sheet under a prescribed air pressure differential between the two surfaces of a material. It is generally expressed in SI units as $cm^3/s/cm^2$.

Air Permeability standard ASTM D737-96, entitled "Standard Test Method for Air Permeability of Textile Fabrics" as established by ASTM International, West Conshohocken, PA, 2018, provides a useful method of quantification of air permeability.

Where air permeability values are set forth hereon, the test pressure is 100 Pa and the air volume is 10 liters measured over 10 cm. Air permeability is measured using TEXTEST FX 3300 air permeability tester according to Das et al. (Journal of Engineered Fibers and Fabrics Volume 4, Issue 4-2009, Fiber and Textile Research in India).

The instant sheets prior to perforation (i.e. without the channels of the instant invention), have an air permeability of at least $0.01\ cm^3/s/cm^2$ and as high as $1000\ cm^3/s/cm^2$ Water Permeability Water permeability can be measure by AATCC Test Method 195 (2009). Briefly, a solution is introduced to proximal or distal surface of the sheet sample. A series of indices are calculated to describe the water handling of the sheet material such as wetting time (sec), absorption rate (%/sec), spreading speed (mm/sec), maximum wetted radius (mm), one-way transport capacity also known as accumulative one-way transport index (AOTI) and lastly overall water handling capacity.

Water permeability values, where set forth herein, are established on a SDL Atlas Water Vapor Permeability Tester.

Moisture Vapor Permeability

Moisture vapor permeability (MVP) can be measured by SDL Atlas Water Vapor Permeability Tester according to standard BS 7209.

Water vapor can diffuse through the sheet by simple diffusion through the air spaces within the sheet. This diffusion can be quantified by determining weight loss with the evaporation time of water contained in a vessel as set forth by Manso re al. in American Journal of Materials Science 2016, 6(6): 147-151.

MVO can also be measured as described in U.S. Pat. No. 5,010,833

In a preferred embodiment, the MVP of the instant dressing in the non-perforated areas (i.e. in the area without channels) is at least 100 gms/m²/24 hours, but preferably at least 500 gms/m²/24 hours, and more preferably at least 1000 gms/m²/24 hours, and more preferably still at least 2000 gms/m²/24 hours, and yet most preferably between 2,500 and 6,000 gms/m²/24 hours (e.g. when measured at 37° C. and 100% to 10% relative humidity).

By way of example, the Applicant has discovered that nonwoven rayon with a sheet of a thickness of between 0.05 and 0.25 mm is an especially suitable material from which to manufacture an instant dressing that has an MVP of about 4200 gms/m2/24 hrs (in the non-perforated areas) yet has a tensile strength at break of 5 lbs/inch width (89 Kg/meter width).

In a preferred embodiment, the sheet contains no intervening compartments such as described in U.S. Pat. No. 5,010,833. Written differently, the adhesive is applied directly to the sheet and, other than an optional liner, there are no other material layers. The instant invention allows transpiration and fluid movement without the need for such a intervening compartment, thereby making the instant invention more reliable and easier to manufacture.

Wickability

Wickability can be measured by a vertical wicking test using a vertical wicking tester according to the DIN 53924 method, e.g. as described by Das et al. (Fibers and Polymers 2008; 9: 225-231).

Wickability can be measured by in-plane wicking behavior of the sheet material as determined by measuring the initial wicking rate (g/min) using a gravimetric in-plane wicking tester, e.g. as described by Das et al. (Fibers and Polymers 2008; 9: 225-231).

Channels

The sheets of the instant invention comprise a plurality of channels. Instant dressing can be made to contain one type of channel (e.g. generally one size, shape, and angle) or two or more channel types (e.g. two different sizes or shapes or angles). Without being bound by theory, optimal exchange functions (e.g. liquid and air exchange), as discovered in the mind of the inventor, can be achieved by using two different types of channels configured and referred to herein as "air channels" and "liquid channels". These names do not indicate exclusivity—i.e. that a liquid channel can only allow trans movement of liquid to the exclusion of air, but rather that the liquid channel have properties that are especially useful for passing liquid (e.g. larger, or facilitate capillary action). Channels, as used herein, are meant to be distinguished from pores which can be part of the sheet material itself (e.g. woven fabric).

A dressing of the present invention can have channels of two different sizes. For example, the dressing can have larger liquid channels (e.g. liquid channels 5, FIG. 1A) and smaller air channels (e.g. air channels 7, FIG. 1A).

Non-perforation zones.

Figure 13:
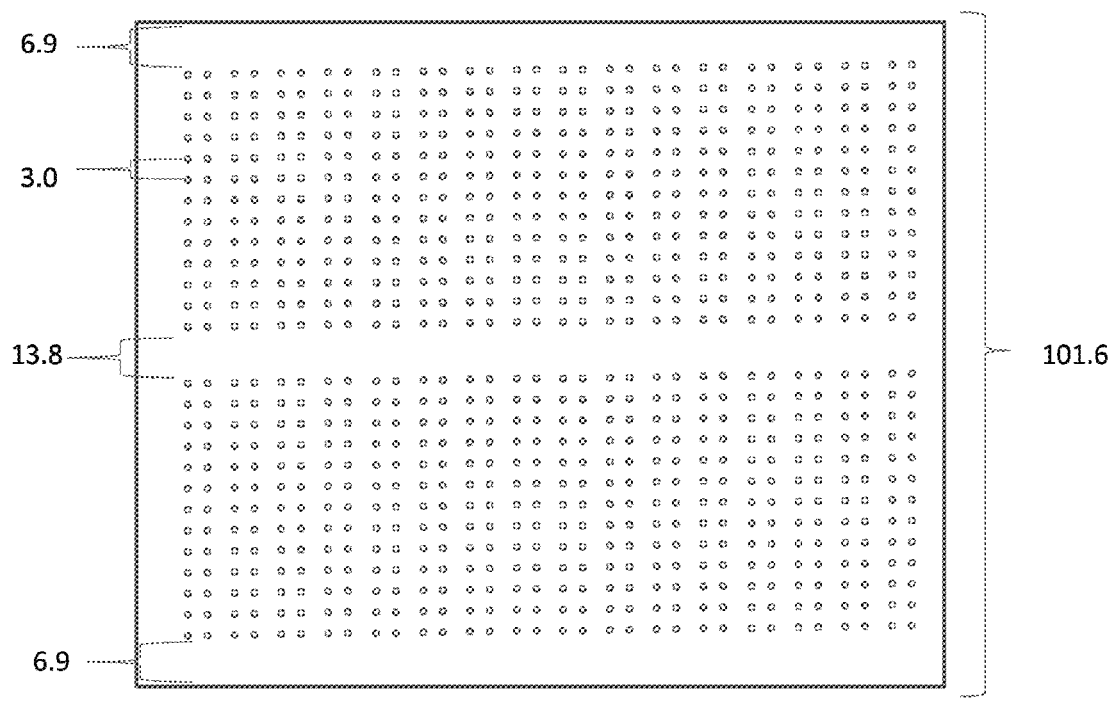
FIG. 13 shows an instant dressing with a non-perforation zone positioned between two channel zones.

Optionally, the instant dressings contain non-perforation zones, i.e. zones where there are no channels that are large enough to effectively facilitate exchange functions taught herein (e.g. larger than 25 µm extending completely through the sheet). Optionally, such regions are provided about the periphery of the sheet. For example, optionally the sheets comprise non-perforated zones within about 2 mm of the periphery measured along the width; optionally, within about 3 or 4 or 5 mm or more of the periphery measured along the width. In other embodiments there are non-perforated zones within about 2 mm of the periphery measured along the length; optionally, within about 3 or 4 or 5 mm or more of the periphery measured along the length. In other embodiments, there are non-perforated zones within about 2 or 3 or 4 or 5 mm or more measured along the width and the length. An example of such a non-perforated zone is zone 1 in FIG. 1. In other embodiments, especially dressing where the width is 4 inches or greater, there is one or more non-perforation zones interspersed between channel zones as illustrated in FIG. 13. It has been discovered here that the non-perforation zones along the periphery of the width of the sheet facilitated superior adherence to the skin and surprisingly, to such an extent that the dressing stays in place on the skin for 2 or 3 weeks or longer.

It has also been discovered that instant dressing that contain larger widths (e.g. 4 inches or more), if they don't also have a non-perforation zone running parallel with the width but at a position other than at the periphery of the dressing, are apt to tear. This, contemplated herein are dressing that maintain the integrity of the sheet by containing one or more non-perforation zones positioned between perforation zones. For example, see FIG. 13

Diameter

The channels can be any size ranging from 25 µm to 10 mm. Optionally, the channels can have a diameter of 50 µm to 3 mm. Optionally, the channels can have a diameter of 50 µm to 2 mm. Optionally, the channels can have a diameter of 100 µm to 2 mm. Optionally, the instant sheet comprises channels of two different diameters.

Density and Numbers

Depending upon intended usage, the channels of the instant invention are at a density ranging from one to about 160,000 every $cm^2$, depending also upon channel size. For example, channels of a diameter of 250 to 1000 µM can optionally be at a density of 1 to 1,600 channels per $cm^2$. Optionally, channels having a mean diameter from about 1-3 mm in the instant invention are at a density of about one to about 100 channels per $cm^2$. Optionally, channels having a diameter of 250 to 1000 µM can optionally be at a density of 1 to 1,600 channels per $cm^2$. Chanel density and channel diameter must be configured such that less than 40% of the surface area defined by the channels is less than 40% of the total surface area defined by the sheet;

Optionally, the instant channels have are at a density such that the aggregate surface area defined by the channels is at least 0.01% of the total surface area defined by the sheet; optionally it is about 0.1% to about 20%; optionally about 1% to about 10%. Additionally or alternatively, the sheet comprises a portion comprising the channels, wherein the aggregate surface area defined by the aperture of the channels that are in the portion is between 0.5% and 30% of the total surface area defined by the portion, e.g. about 0.2% to about 20%. Optionally, the portion is a grid of channels (e.g. as shown in FIG. 3).

Figures 3A, 3B:
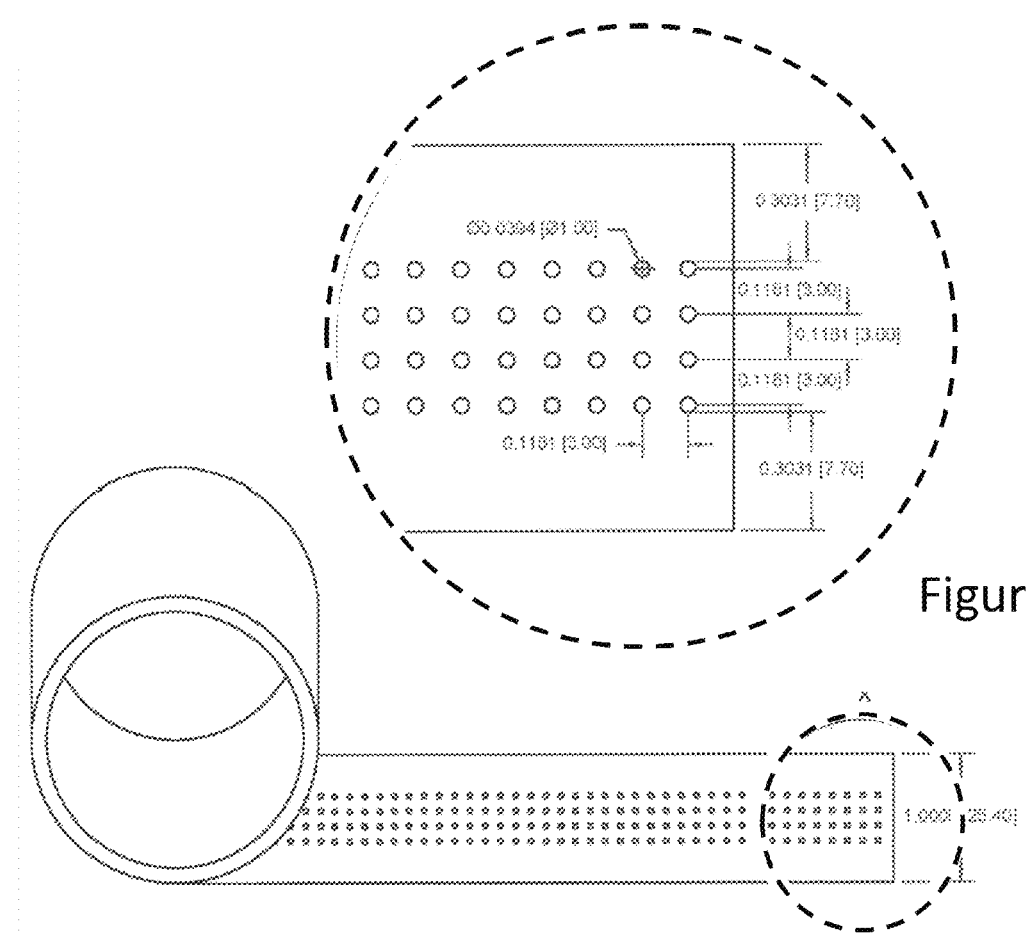
FIG. 3A shows one embodiment of the instant invention.
FIG. 3B is a partial view thereof. The parenthetical numbers are millimeters and the other numbers are inches.

The following is an example of calculating aggregate surface area defined by channels The partial view shown in FIG. 3 has an 8×4 grid of channels (32 channels). Each channel has a diameter of 1 mm (area of 0.5 mm×0.5 mm×3.1416=0.7854 mm$^2$). The aggregate surface area of the channels is 25.133 mm$^2$ (32×0.7854 mm$^2$). The grid of channels is a portion of the sheet comprising channels. With 3 mm channel spacing (center to center), the grid has a length of 22 mm and a width of 10 mm (220 mm$^2$). Accordingly, the aggregate surface area defined by the channels divided by the surface area of the channel zone is 25.133 mm$^2$/220 mm$^2$ (11.42%). The aggregate surface area defined by the channels divided by the total surface area of the sheet (i.e., the channel zone plus the non-perforation zone) is about 4.5%.

Shape

The instant channels can be configured in a manner to optimize exchange functions. It has been discovered in the mind of the inventor that by configuring size, shape, angle, and density of channels, that vapor permeability, water permeability, wickability, and air exchange can be optimized such that healing of a wound is unexpectedly facilitated.

Among the channel shapes that augment such exchange functions are tapered (e.g. conical shape), elliptical shape (e.g. elliptical prism shaped), cylindrical shape, and star shape (e.g. star prism shaped).

Star shaped channels have portions that are optimized for air exchange and other portions that are optimized for liquid exchange.

The functionality optimizations of other shapes are discussed more fully under the Liquid Channel subsection herein.

Air Channels

Optionally, the channels of instant invention comprise a first channel type which are channels designed to facilitate the exchange of gasses and air from the proximal side of the sheets to the distal side, and from the distal side of the sheets to the proximal side. Air channels are configured into the sheet at a density, size, shape, and orientation, depending upon the purpose, as described in "Exemplary Embodiments" below.

The channels of the first channel type have a diameter of 25 µm to about 2,500 µm or optionally, a diameter of 25 µm to about 2,500 µm. or optionally, a diameter of 25 µm to about 1,000 µm, or optionally, a diameter of 25 µm to about 300 µm.

Optionally, these air channels have a channel density such that the aggregate surface area defined by the channels is at least 0.01% of the total surface area defined by the sheet; optionally it is about 0.1% to about 20%; optionally about 1% to about 10%. Alternatively, where the sheet comprises a non-perforated zone, these air channels have a density of at least 0.01% or have a density of about 0.1% to about 20% or optionally about 1% to about 10% as defined by the area of the channel zone.

Liquid Channels

Optionally, the channels of instant invention comprise a second channel type which are channels designed to facilitate the exchange of liquids from the proximal side of the sheets to the distal side, and from the distal side of the sheets to the proximal side. Liquid channels are configured into the sheet at a density, size, shape, and orientation, depending upon the purpose, as described in "Exemplary Embodiments" below. Such channels of the second channel type can be provide independently or in combination with channels of the first channel type.

The channels of the second channel type have a diameter of 250 µm to about 10,000 µm or optionally, a diameter of 500 µm to about 2,500 µm. or optionally, a diameter of 800 µm to about 2,000 µm, or optionally, a diameter of 750 µm to about 1,500 µm.

Optionally, liquid channels have diameter of at least about 1 mm (e.g. 1 mm to about 4 mm). For example, FIG. 1A depicts liquid channels 5 having a diameter of 1 mm, and also depicts another embodiment in which the liquid channels are 1.5 mm in diameter, and also depicts another embodiment in which the liquid channels are 2.5 mm in diameter.

Optionally, the instant liquid channels have a channel density such that the aggregate surface area defined by the channels is at least 0.01% of the total surface area defined by the sheet; optionally it is about 0.1% to about 20; optionally about 1% to about 10%. Alternatively, where the sheet comprises a non-perforated zone, these liquid channels have a density of at least 0.01% or have a density of about 0.1% to about 20% or optionally about 1% to about 10% as defined by the area of the channel zone.

Shape

The instant channels of the second channel type (liquid channels) can be configured in a manner to optimize capillary action. It has been discovered in the mind of the inventor that such capillary action-optimized channels further facilitates wound repair. For example, capillary action is increased when the channels are not perpendicular to the sheet, but at an angle, increasing the length of the channel through the sheet (e.g. the center or edge of the channel opening on the distal side is laterally offset from the center or edge of the corresponding channel opening on the proximal side).

Another capillary action-optimized channel is a channel in the shape of a cone, or other tapered channel. Dressings of the instant invention facilitate the movement of liquids from the distal side (e.g. topical agents) to the proximal side and liquids from the proximal side (e.g. exudates) to the distal side, cone-shaped channels of the instant invention are oriented in both directions (i.e. the larger diameter side of the cone oriented towards the distal side in some instance and towards the proximal side in other instances).

Another capillary action-optimized channel is elliptical in shape.

Optionally, channels of the instant invention comprise two or more of conical channels, elliptical channels, cylindrical channels, or star-shaped channels.

Optionally, capillary action-optimized channels of the instant invention have a diameter of less than 3 mm or less than 2 mm.

Adhesive Layer

The adhesive can be any dermatologically acceptable adhesive or glue. For example, the adhesive is pressure sensitive. Optionally, the adhesive is organic.

Suitable adhesives are known to be useful for application to skin. A suitable class of adhesives is disclosed, for example, in U.S. Pat. No. 6,441,092 (Gieselman). One example is a blend of 85 weight percent of 2-ethylhexyl acrylate/acrylic acid/ABP (96.5/3.5/0.05 weight ratio) and 15 weight percent Avalure AC 210 acrylate copolymer adhesives containing from about 5 to about 20 weight percent of such hydrophilic materials provide a good balance of desired moisture permeability without unduly softening the adhesive layer to yield undesirable levels of residue.

The adhesive can be a pressure sensitive adhesive, which is a viscoelastic material that displays aggressive tackiness and adheres well to a wide variety of substrates after applying only light pressure (e.g., finger pressure). One well-known means of identifying pressure sensitive adhesives is the Dahlquist criterion. This criterion defines a pressure sensitive adhesive as an adhesive having a 1 second creep compliance of greater than $1 \times 10\text{-}6$ square centimeters per dyne (cm2/dyne) as described in Handbook of Pressure Sensitive Adhesive Technology, Donatas Satas (Ed.), 2nd Edition, p. 172, Van Nostrand Reinhold, New York, N.Y., 1989;

Other illustrative examples of useful adhesives include those described in U.S. Pat. No. 4,112,177 (Salditt et al.), particularly the tackified acrylate "skin layer adhesives" described in Example 1; U.S. Pat. No. 5,648,166 (Dunshee), RE 24,906 (Ulrich); U.S. Pat. No. 4,737,410 (Kantner) (see example 31); U.S. Pat. No. 3,389,827 (Abere et al.); U.S. Pat. No. 4,112,213 (Waldman); U.S. Pat. No. 4,310,509 (Berglund et al.); U.S. Pat. No. 4,323,557 (Rosso); U.S. Pat. No. 6,083,856 (Joseph et al.); and U.S. Pat. No. 6,497,949 (Hyde et al.); and U.S. Patent Application Pub. Nos. 2002/0165477 (Dunshee) and 2002/0193724 (Stebbings et al.).

Another especially useful adhesive is that tackified acrylate taught in United States Patent Application No. 20170362468.

The adhesive can optionally comprise a pressure sensitive rubbery elastic material having intimately dispersed therein one or more water soluble or water swellable hydrocolloids. Suitable rubbery elastomers include natural or synthetic viscous gum-like substances such as natural rubber, silicone rubber, acrylonitrile rubber, polyurethane rubber, polyisobutylenes, etc., with a mixture of polyisobutylenes of a molecular weight of 5,000 to 11,700 and 81,000 to 99,000 being preferred (these are commercially available as Vistanex and Hyvis). Suitable hydrocolloids include guar gum, sodium carboxymethylcellulose, cross-linked sodium carboxymethylcelulose, pectin, gelatin, alginic acid, locust bean gum, karaya, etc. The viscous gum-like substance acts as a binder for the hydrocolloid particles and, in addition, renders the final adhesive layer tacky, elastic, and pliable.

The hydrocolloid or mixtures of hydrocolloids can optionally comprise from about 20% to 65% by weight of the adhesive layer, optionally from about 30% to about 60% by weight of the adhesive layer. The elastic materials can optionally comprise from about 30% to 60% by weight of the adhesive layer, preferably from about 35% to 50% by weight of the adhesive layer.

The adhesive can optionally include up to about 35% by weight of one or more tackifiers, plasticizers or solvents, antioxidants, and preservatives. Suitable tackifiers, by way of example, include terpene resin, a starch-acrylonitrile graft copolymer (such as that commercially available as Poly 35A-100), or a copolymer of polyvinylpyrrolidone and vinylacetate. Suitable plasticizers or solvents include mineral oil, paraffin wax, and petrolatum with mineral oil being preferred. Suitable antioxidants include butylated hydroxytoluene (BHT), which is preferred, and butylated hydroxyanisole (BHA).

The adhesive layer in dressing can be at any suitable thickness. By way of example, the adhesive layer can vary from about 50 μm to about 250 10 μm in thickness and can optionally comprise pores of from about 10 microns to about 300 microns in size.

Optionally, the adhesive layer can be formed in parallel adhesive lanes as described in U.S. Pat. No. 9,877,874, incorporated by reference here.

Examples of useful adhesives according to the instant invention are those utilizing acrylate, block copolymer (e.g., adhesives based on KRATON polymers commercially available from Kraton Polymers, Houston, Tex.) and rubber based pressure sensitive adhesives. Examples are tapes and dressings commercially available from 3M Company under the trade designations TRANSPORE, BLENDERM, STERISTRIPS, MICRO PORE, TEGADERM, STERID RAPE, and IOBAN II.

Sheet—Adhesive Embodiments

Examples of sheet-adhesive layer combinations useful according to the instant invention are microporous tapes, e.g. a paper tape. A useful porous tape is sold by 3M under the trade mark "MICROPORE".

Topical Agents

In one embodiment, the dressings of the instant invention further comprise a topical agent. Optionally, the topical agent is disposed on the same side of the sheet as the adhesive is bound to. Optionally, the agent is impregnated throughout the sheet.

In another embodiment, one or more topical agents is applied directly to the skin, a wound, an injury, or a suture and the instant dressing is applied over the skin, etc.

In another embodiment, the one or more topical agents are admixed with an adhesive solution or liquid and the mixture is applied to the wound area. Optionally, the wound area includes the periphery of the dressing thereby reducing the likelihood of the dressing becoming unattached to the wound area at the periphery.

The topical agent can be anti-acne agents, anesthetics, anti-infectives, anti-rosacea agents, antibiotics, anti-cancer agents, anticoagulants (of the small molecule type, biologic type, as well as chemical-type such as aluminum chloride). antifungals, antihistamines, antineoplastics, antipsoriatics, antivirals, astringents, debriding agents, depigmenting agents, emollients, keratolytics, a non-steroidal anti-inflammatoy agent, an antihistamine, and a local anesthetic photochemotherapeutics, rubefacient, steroids, steroids with anti-infectives, a wound astringent healing promoter, a hemostatic, a sterilizer or a disinfectant.

In one embodiment, the topical agent is one or more natural biologic agents.

Specific examples of sterilizers or disinfectants include chlorhexidine gluconate, benzalkonium chloride, chloroxylenol, acrinol, thianthol, dequalinium chloride, sulfisomidine, sulfamine, nitrofurazone, boric acid, homosulfamine, and triclocarban. Examples of the healing promoter include zinc oxide, pyridoxine hydrochloride, tocopherol acetate, and pyridoxine dipalmitate. Examples of the hemostatic agent include naphazoline hydrochloride, zinc sulfate, and ephedrine hydrochloride. Examples of anti-inflammatory agents include steroids such as prednisolone, dexamethasone, cortisone acetate and other steroids, glycyrrhetinic acid, and lysozyme chloride. Examples of antihistamines include chlorophenilamine maleate and diphenhydramine hydrochloride. Examples of local anesthetics include lidocaine, ethyl aminobenzoate, procaine hydrochloride, dibucaine hydrochloride, tetracaine hydrochloride, and diethyl aminoethyl p-butylamino-benzoate hydrochloride.

Antifungal Topical Agent

A topical agent can be any topical antifungal agent and by way of example, any topical imidazole, triazole, thiazole (e.g. abafungin), allylamine, or echinicandins topical antifungal agents.

Examples of useful imidazole topical antifungal agents are bifonazole, butoconazole, clotrimazole, econazole, fenticonazole, isoconazole, ketoconazole, luliconazole, miconazole, omoconazole, oxiconazole, sertaconazole, sulconazole, and tioconazole antifungal agents.

Examples of useful triazoles topical antifungal agents are albaconazole, efinaconazole, epoxiconazole, fluconazole, isavuconazole, itraconazole, posaconazole, propiconazole, ravuconazole, terconazole, and voriconazole antifungal agents.

Examples of useful allylamine topical antifungal agents are amorolfin, butenafine, naftifine, and terbinafin antifungal agents.

Examples of useful echinocandins topical antifungal agents are anidulafungin, caspofungin, and micafungin antifungal agents.

Examples of other useful topical antifungal agents are aurones, benzoic acid, ciclopirox, flucytosine m griseofulvin, haloprogin, tolnaftate, undecylenic acid, crystal violet, balsam of peru, orotomide, and miltefosine.

Antimicrobial Topical Agent

An antimicrobial topical agent can be, e.g. an antibiotic. An antibiotic, useful according to the instant invention, can be any antibiotic.

By way of example, colistin is a member of a polymyxin family of antibiotics. Colistin is a member of a group of antibiotics known as polycation antibiotics. Colistin is a member of a group of antibiotics known as peptide antibiotics. Colistin is a member of a group of antibiotics known as aminoglycoside antibiotics. The structural features of members of these antibiotics (i.e. aminoglycoside antibiotics, polycation antibiotics, or peptide antibiotics) allow them bind to lipopolysachharides (lps) of bacteria and alter packing arrangement, leading to death. Without being bound by theory, it is believed that this common structural and function feature serves a role in antibiotic action (bacterial killing) and antibiotic resistance and is the target for overcoming resistance by Apyrase Agent.

As used herein, "colistin-type" antibiotics include, e.g., alpha defensin (NP-1), bacitracin, bactenecin, Beta defensin 1, buforin II, cecropin A, cecropin P1, Colimycin, gentamycin, Gramicidin S, indolicidin, magainin II, nisin, polymxin B, ranalexin, tachyplesin, and tobramycin.

With the teaching herein, the skilled artisan should immediately appreciate that all references herein to "colistin" apply equally to "colistin-type" antibiotics.

Examples of other antibiotics useful according to the instant invention antimicrobial polymer E2, antimicrobial polymer E4, macrolides, polymyxins, penicillin, cephalosporin, carbepenem, monobactam, beta-lactam inhibitor, oxaline, aminoglycoside, chloramphenicol, sulfonamide, glycopeptide, quinolone, tetracycline, fusidic acid, trimethoprim, metronidazole, clindamycin, mupirocin, rifamycins, streptogramin, lipoprotein, polyene, azole, or echinocandin. Additional specific antimicrobials that find use within the scope of the technology are erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin.

Anticancer Agents

An anticancer topical agent can be any anticancer agent that is useful in topical formulation. examples of classes of anticancer drugs are cytotosic nucleoside analogues, antifolates, topoisomerase i inhibitor, podophyllotoxins, anthracyclines, taxanes, vinca alkaloids, alkylating agents, platinum compounds, tyrosine kinase inhibitor, m TOR inhibitors, retinoids, histone deacetylase inhibitors, and the like.

Natural Biologics

Natural biologics can be added to the instant dressing or to the wound and the instant dressing applied over the wound or the natural biologic can be added to the distal side of the instant dressing (before or after application to the wound. By way of example, an instant natural marine extract can be an extract described by Lewis in U.S. Patent Publication No. US 2014/0106001.

Protective Material

The instant dressing optionally comprises a protective layer releasably secured on the proximal side or distal side of the instant dressing, or a protective layer on both sides. The protective layer is to be removed before application of the instant dressing to the wound, e.g. configured as a peelable protective layer.

Such a protective layer prevents the instant dressing from adhering to any packaging material (e.g. an envelope) or to itself in the embodiment where the dressing is in the form of a roll.

The protective layer can comprises a first side and a second side, wherein the first side (e.g. side 2 of protective layer in FIG. 1), contacts the proximal or adhesive side of the sheet, and the second side does not come in contact with the sheet (e.g. side 6 of protective layer in FIG. 1).

The protective layer may be formed from any material which facilitates release from the adhesive layer or the distal face of the dressing. For example, the protective layer can be polyvinyl chloride, or any other synthetic resin. The protective layer may also be provided at one end with a slit which facilitates its removal.

The protective layer can optionally be craft paper, polyethylene, polypropylene, polyester or composites of any of these materials.

The protective layer can be coated with release agents such as fluorochemicals or silicones. For example, U.S. Pat. No. 4,472,480 describes low surface energy perfluorochemical liners. The protective layers can be papers, polyolefin films, or polyester films coated with silicone release materials. Examples of commercially available silicone coated release papers are POLY SLIK™, silicone release papers and other silicone release papers supplied by Loparex Inc. (Willowbrook, Ill.).

Medical Use

In one embodiment, the instant dressing is applied over a wound. Optionally, the instant dressing is left in place for one or more days while the wound is healing; e.g. 5 or more days or 10 or more days or 15 or more days or 20 days or more days. Optionally, the subject is instructed to allow the dressing to remain applied until the dressing falls off unaided.

In one embodiment, the instant dressing is applied over a suture.

In another embodiment, skin is treated with a topical medicament and the instant dressing is applied over the treated skin.

In another embodiment, the wound is prepared according to any standard care, the dressing is applied, and then the wound is periodically (e.g. daily or every other day (or more or less frequently) washed or treated with a topical medicament, In another embodiment, avulsions are treated with instant dressings, with or without integral antibiotic or antimicrobial topical agents (i.e. dressings produced with topical agents) or with or without such topical agents added to the distal side of the dressing after the dressing is applied to the wound. The dressing is left on the wound undisturbed for periods as long as three weeks or longer.

In another embodiment, instant dressing is applied prophylactically to skin in areas that are prone to wounds such as pressure sores or other friction-caused sores.

In another embodiment, instant dressing is applied for patients with recurrent nose bleeds.

In another embodiment, postoperative scars are treated by a method of applying an instant dressing to the scar running along the length of the scar.

One example of medical use of the instant invention is the application of the instant dressing over a suture following a surgical incision.

In another example, the instant dressing is applied over an incision that has not been closed by a suture or other closure means. In this case, the dressing serves as a means to close the suture and aid the natural wound repair mechanisms.

One example of medical use of the instant invention is the application of the instant dressing to localized cancers or pre-cancerous areas wherein the dressing contains anticancer agent such as 5-FU. By way of example, such cancers and pre-cancers can be those of the skin, mouth, nose, bladder, vagina, cervix, or lips.

Another example of medical use of the instant invention is application of the instant dressing over a punch biopsy.

Another example of medical use of the instant invention is application of the instant dressing over a wart, wherein the dressing can optionally be produced to contain keratolytic agents such as salicylic acid (without or without lactic acid) or uric acid, or the like.

Another example of medical use of the instant invention is application of the instant dressing for long-term care, e.g. stoma, ostomy care, amputee care, feed tubes, ventral catheter, cutaneous lines, and intertracheal tube care.

Another example of medical use of the instant invention is application of the instant dressing over insect bites, wherein the instant dressing also provides a means of treating the bite with anti-itch compounds such as hydrocortisone.

Another example of medical use of the instant invention is application of the instant dressing over abrasions, wherein antimicrobial agents (e.g. polysporin/Neosporin, etc.) can also be applied. If bleeding continues to occur or exudates continue, hydrogen peroxide can be applied to the distal side of the dressing.

Another example of medical use of the instant invention is application of the instant dressing over bruises wherein the dressing can stabilize the skin to speed healing and minimize further bruising and post-inflammatory hyper-pigmentation. Such hyper-pigmentation can be treated by using an instant dressing comprising hydroquinone or by adding hydroquinone to the distal side of the dressing or both.

Another example of medical use of the instant invention is application of the instant dressing over skin tears. Indeed, certain fragile skin (resulting from age or a medical condition) are poor candidates for suturing. Surprisingly, it has been discovered that the instant dressing can facilitate wound healing without sutures.

Another example of medical use of the instant invention is application of the instant dressing over areas of continuous friction that tend to get pressure sores. Such areas can be treated with topical agents, either by direct incorporation in the dressing or by application to the distal side of the dressing before application or to the distal side of the dressing after application. Examples of such use are bed sores and pressure sores from wheel chairs.

Another example of medical use of the instant invention is an instant dressing that is configured in a manner for mucosal use; by way of example, for mouth, throat, nose, and vaginal application. It has been discovered in the mind of the inventor that the instant dressing are especially useful for application to the gums to treat or prevent ulcers of the gums from dentures, It has also been discovered that the instant dressing provide superior care for patients with genetic or acquired skin sensitivities; e.g. Steven Johnson Syndrome, erythema multiforme, or dystrophic epidermolysis bullosa.

The instant dressing can also be configured in a manner for internal use; by way of example, for stomach, bladder, and the like.

The instant dressing is also useful for diverse application of superficial traumatic and surgical wounds, providing greatly reduced or eliminating totally the requirement for post-operative care.

It has also been discovered, based upon an assessment of embodiments of the instant invention, that instant dressings have special usefulness in more extreme situations such as the battlefields, wilderness, and even in open water.

In some embodiments, the instant dressing is manufactured in widths greater than, e.g. 20 or 30 cm. This form is especially useful for covering burns or bed sores.

Other uses of wide instant dressings are for applying to eczyma, psoriasis, and other extensive inflammatory rashes.

Wide instant dressing are also useful for application to generalized body erosions/ulcers, penphigris, pemphrgoid, burns, Steven Johnson Syndrome, erythema multiforme, herpes symplex, epidermolysis bullosa, Grover's, Haily-Haily. In one embodiment, the dressing is left on the skin until it falls off (e.g. in three weeks), thus eliminating daily wound changes and wounds sticking to sheets which would otherwise be painful. These patients can soak in baths to clean wounds through the instant dressing. The instant dressing protects against scratching, further damaging skin while water emersion cleans the wound.

In another embodiment, the instant dressing is used in veterinarian medicine. Animals such as companion animals (e.g. dogs and cats) are known to be generally intolerant of dressings and through licking and biting actions, attempt to remove them. It has been discovered in the mind of the inventor, that presumably because of increased breathability and vapor transpiration), animals are often more tolerant of the instant dressing.

Various Forms

The instant dressings can be produced in any form useful in the medical arts. For example, it can be produced as a roll. Optionally, the dressings can be segmented (e.g. perforated segment 3, FIG. 1a) for ease of tearing to the desired length. Optionally, the roll can be on a dispenser. Optionally, the dressings can be sterile. Optionally, the dressings can be in various widths and lengths and shapes and packaged in a sealed envelope-like package.

Problems Being Solved

Dressings are typically applied to wounds in order to protect the wound surface, absorb fluids exuded from the wound and to let air into the surface of the wound. However, it is important to prevent the contamination of the wound without impeding the progress of the natural healing process of the body, and in some cases, to protect the environment against contamination from the wound.

It is also important to avoid, or at least impede, the formation of an adherent bond between the wound surface and the dressing; such a bond can be formed when the body fluids exuded from the wound into the dressing dry to a crust and the dry crust adheres to the healing flesh and to the dressing. This makes very difficult the removal of the dressing without causing great pain to the patient and, even more important, without reopening a partially healed wound.

In an attempt to prevent an adherent bond between a wound and a dressing, manufacturers have added silicone or other non-stick materials to the dressing sheet material. By way of example, the TEFLA™ "ouchless" bandage is advertised as not sticking to a wound. However, such non-stick dressings are known to "suffocate" wounds and causes maceration, wound disruption, and potential infection in many use scenarios. In preferred embodiments of the instant invention, the dressing contains less than 20% or less than 10% less than 1% or no silicone (e,g, polydimethylsiloxane) or polytetrafluoroethylene (PTFE) or synthetic fluoropolymer of tetrafluoroethylene or other synthetic polymeric materials.

Modern practice of applying dressings, removing dressings, and reapplying fresh dressings are fraught with other problems. This process is known to the inventor to cause mechanical disruption. For example, skin (or epidermal) stripping can occur, where one or more layers of the stratum corneum are removed following removal of adhesive tape or dressing. The resulting lesions are typically shallow and irregular in shape. Erythema and blister formation often accompanies skin stripping. Tension injuries or blister (i.e. separation of the epidermis from the dermis) can result from shear force resulting from distention of skin under unyielding adhesive tape. Skin tear can also occur by shear or friction causing separation of skin layers.

Maceration, that is, changes in skin resulting from moisture being trapped against the skin for prolonged periods of time is a typical result of use of dressings. This results in softening of the skin and increased permeability and susceptibility to damage from irritants or friction. Such maceration can occur with typical dressing in the art, even those that do not contain synthetic polymeric sheet materials.

Dermatitis is also a frequent problem which occurs when using dressings (more typically, with adhesive backed dressings). Irritant contact dermatitis and allergic dermatitis are frequently observed.

In certain conditions such as burns and other extensive wounds, it is useful to protect pain centers.

Each of these problems (i.e. mechanical disruption, dermatitis, burns, various wounds, and maceration) are exacerbated in the elderly. Other factors that can worsen these problems are diabetes, infection, renal insufficiency, immunosupression, venous insufficiency, venous hypertension, and peristomal varices, malnutrition, and dehydration. There has been a long recognized need for a solution to these problems.

A further problem is absorbing the body fluids which tend to exude from a wound so as to remove the fluids from the surface of the wound, permitting it to dry; this furthers the healing process; it is also necessary at the same time to control the loss of fluid. It is most advantageous, especially when dealing with massive burns, to insure against shock by preventing the excessive loss of the salts from the body which generally are dissolved in any body fluids which may be exuded. Therefore, by limiting the loss of body fluids, the loss of salts is also impeded, thereby decreasing the chances of severe shock.

Due, in part, to the problems set forth above, dressings of the medical art require periodic removal and replacement. Such removal brings at least two additional problems. First is one of patient compliance. Patients are often forgetful or reluctant to attend to their own wounds. This results in further failure of the dressing to function in the desired manner. A second problem is that when bandages are removed, the removal can cause a disruption healing process. It is well understood that healing involves sequential stages of homeostasis (e.g. Infiltration of platelets, activation of fibrin, and clotting), inflammation (e.g. phagocytosis of damaged and dead cells and pathogens and debris), proliferation (angiogenesis, collagen deposition, granulation tissue formation, epithelialization, and would contraction), and maturation (remodeling). The removal of dressings, made necessary by dressing failure (e.g. saturation by exudates or attachment of eschar) also removes cellular tissue essential for normal wound repair.

Through insight of the inventor, the instant invention had arrived at a balanced solution to each of these problems. For example, the instant dressing provides all of the usual attributes of a surgical dressing, including the ability to absorb the body fluids exuded from the wound, to protect the wound surface, to permit the transpiration of air and moisture between the atmosphere and the wound surface, and a long term functionality without failure. The inventor has discovered that the unique combination of microporous sheet material and macro-channels results in functionality that are not present in any one of the dressings of the prior art. Additionally, the instant dressings impede the passage of microorganisms to or from the wound surface while retaining the ability to permit full transpiration of air and moisture during use.

The instant dressings are especially useful for large open wounds or massive burn areas, where there is heavy exudation of body fluids from the skin. The nature of the sheet (i.e. allowing some air and liquid to pass), when combined with the channels (optimized for passing liquid and air), surprisingly provide a means to prevent the loss of bodily fluids and salts and maintain the wound or burn area aseptic and free from dirt, dust or other contaminants or irritants.

The instant dressings have a large capacity to absorb exuded body liquids without permitting loss of such liquids through the upper layer of the dressing, thus controlling the loss of fluids and the salts dissolved therein from the body.

The instant dressings provide an open passage for the atmosphere to the space within the dressing, and especially that immediately above the wound.

The instant dressings are sufficiently porous to permit the passage of air at a substantially zero pressure differential across the surface. The dressing does not pass the air by a diffusion process, as in the case of a membrane, but rather by direct air flow through open pores.

The instant dressings have a fluid flow capacity sufficient to maintain transpiration over the entire covered area.

With the instant invention, it is no longer necessary to non-stick portions of dressing that can suffocate wounds, causing maceration, wound disruption, and potential infection.

The instant dressings can withstand typical abrasions to which they may be subjected during use. Instant dressings have sufficient wear resistance to maintain their usefulness over a period of time when worn by an active patient.

In one form of the instant invention, the dressings have a width that is 30 cm or greater. Such a form is especially useful where there are large areas of the skin in need of protection and topical treatment. For example, the current medical treatment poorly meets the needs of patients with conditions involving large body erosions, ulcers, eczyma, psoriasis, inflammatory rashes, penphigris, pemphrgoid, Steven Johnson Syndrome, erythema multiforme, herpes symplex, epidermolysis bullosa, Grover's, Haily-Haily, burns, etc. These conditions can be very painful and require daily changes of standard dressings of the art due to poor handling of exudates and inability to otherwise provide periodic topical agents. With the instant dressing, the bandages can surprisingly treat the above conditions in an effective manner. The instant bandages can be left in place and allow exchange of air and liquids, allow the periodic application of topical agents, and do not subject the patient to the pain and tissue destruction of daily bandage changes. Moreover, patients can soak in baths to continue to clean the wounds and relive discomfort and paint. In addition to the application of topical agents taught elsewhere herein, in some cases it is useful to apply coagulants and anesthesia. For wounds and optionally large wounds, adding elastic components to the instant sheets can help control active bleeding.

Method of Manufacture

In one embodiment, large sheets are passed over a roller (e.g. rolling die 13, FIG. 2) after being coated with adhesive, using high pressure to laminate the adhesive to the sheet. When the adhesive dries, channels are cut into the laminate.

Figure 2:
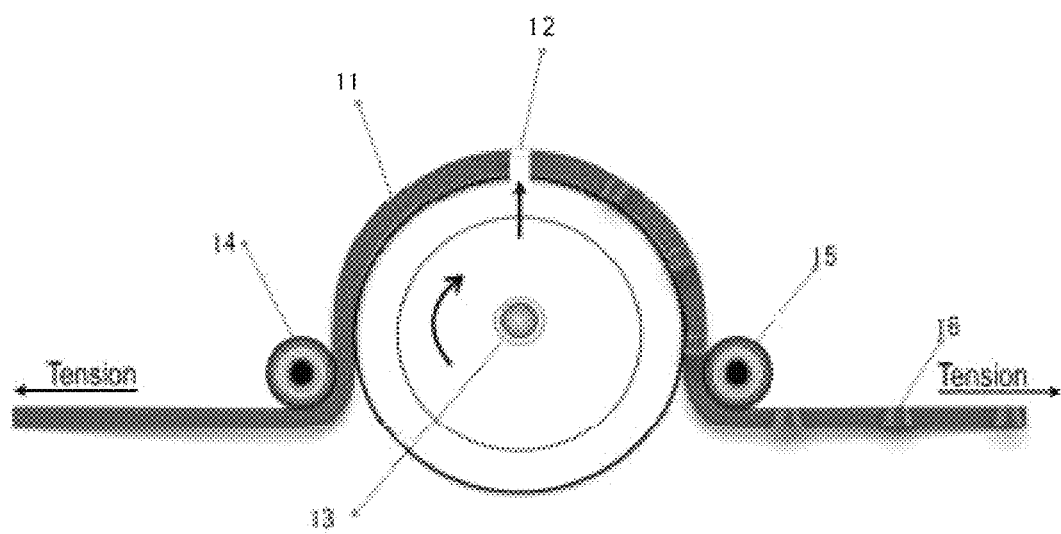
FIG. 2 shows one method of forming channels in the instant sheets

Channels can be cut by any means, for example, by punching (e.g. using punch 12, FIG. 2). For example, channels can be cut by passing a sheet over a roller having a punch(s) projecting therefrom, i.e. a punch roller. One such method is illustrated in FIG. 2, in which sheet 11 is passed under a rear tension roller 14, over a punch roller 13 (e.g. rolling die), and under a forward tension roller 15.

The various shapes of channels can be produced by changing the shape of the punch or the angle of the punch.

Elliptical channels can be produced with cylindrical punches by applying tension to the sheets in one dimension (i.e. stretching in a first dimension relative to a second perpendicular dimension) as they are being passed under the roller.

Tapered channels can be produced by stretching one side of the sheet (e.g. proximal or distal side) relative to an opposing side of the sheet and then punching through the sheet, e.g. by stretching sheet 11 over a roller as shown in FIG. 2 to produce cone shapped channels 16.

The sheets are then cut into widths according to specific applications and typically rolled on a roll.

Dressing Dispensers

Figure 4B:
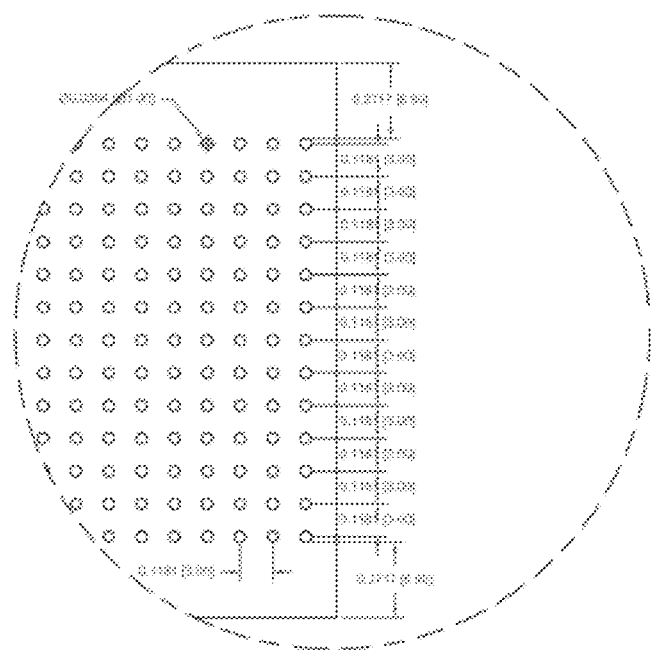
FIG. 4B is a partial view thereof. The parenthetical numbers are millimeters and the other numbers are inches.
Figure 4A:
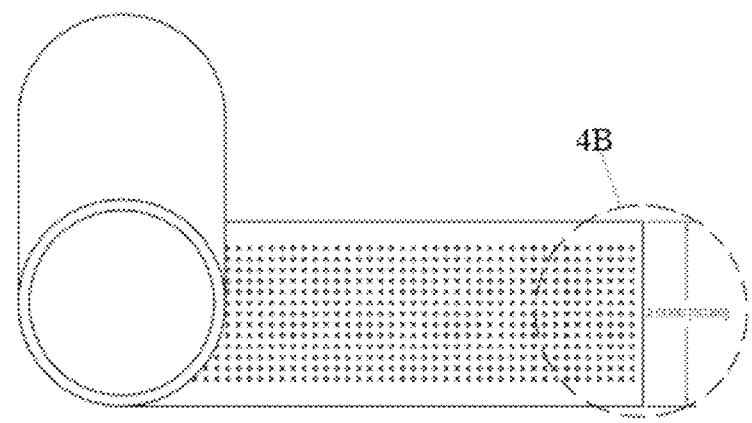
FIG. 4A shows one embodiment of the instant invention.

In one embodiment, the instant dressings are rolled in the direction of the length (e.g. in the shape of a cylinder) and optionally wrapped around a cylinder of an appropriate length (e.g. about the width of the dressing) to form a "roll", e.g. as shown in FIG. 1, FIG. 3, and FIG. 4.

Optionally, the roll is on a dispenser. Non limiting examples of suitable dispensers are those described by Arnold in U.S. Pat. No. 5,171,397 and those described in the background art of said patent. The instant embodiments in a roll and especially on a dispenser are especially useful in that it allows the medical professional to easily dispense the length needed and to cut it to size.

EXEMPLARY EMBODIMENTS

With the teaching described here, the skilled artisan will now readily recognize Exemplary Embodiments and uses of the instant invention. By example, the following embodiments are contemplated.

EE1. A dressing comprising a sheet and an adhesive, wherein:
  a. the adhesive is adhered to the sheet,
  b. the sheet (i) has channels; (ii) is air and water permeable in a portion without the channels; and (iii) has a proximal side comprising a surface area, and a distal side comprising a surface area,
  c. the channels (i) traverse the sheet from the proximal side to the distal side at an angle relative to said sides; (ii) are 1 to 160,000 in number per $cm^2$ of the distal surface area; and (iii) have a diameter of 25 μm to about 10 mm;
  d. the adhesive, the sheet, and the dressing are dermatologically acceptable;
  e. the channel angle is from 20 degrees to 90 degrees (i.e. the angle between the wall of the channel and to surface of the sheet); and
  f. the sheet has a length and a width and wherein the length is equal to or greater in length than the width.

Sheet Composition

EE2. The dressing of EE1 where the sheet is an animal or plant product.

EE3. The dressing of EE1 or EE2 where the sheet comprises synthetic components.

EE3.5 The dressing of EE1 or EE2 where the sheet is a fibrous sheet, optionally wherein the sheet is a woven or nonwoven sheet.

EE4. The dressing of EE1 or EE2 where the sheet is not a thermoplastic or a molded polymer or a rubber or latex product.

EE5. The dressing of any one of EE1-EE4 where the sheet comprises nylon.

EE6. The dressing of EE1 or EE2 wherein the sheet is a cellulosic sheet.

EE7. The dressing of EE6 wherein the cellulosic sheet is a paper sheet, a cotton sheet, or a combination thereof.

EE8. The dressing of any of EE1-EE7 wherein the dressing does not elongate in any direction in an amount more than 10% and recovers at least 55 percent of its elongation.

EE9. The dressing of any of EE1-EE7 further comprising elastomeric materials and wherein the dressing is elastic and elongates in at least one direction in an amount of at least 10% and recovers at least 55 percent of its elongation.

EE10. The dressing of any of EE1-EE7 further comprising elastomeric materials and wherein the dressing is elastic and elongates in at least one direction in an amount of at least 20% and recovers at least 55 percent of its elongation.

EE11. The dressing of any of EE1-EE7 further comprising elastomeric materials and wherein the dressing is elastic and elongates in at least one direction in an amount of at least 30%, 40%, or 60% and recovers at least 55 percent of its elongation.

Channels

EE12. The dressing of any one of EE1-EE11 wherein the channels are 1 to 1000 in number per $cm^2$ of the distal surface area; and have a diameter of 25 μm to about 2.5 mm.

EE13. The dressing of any one of EE1-EE11 wherein the channels are 1 to 500 in number per $cm^2$ of the distal surface area; and have a diameter of 25 μm to about 2.5 mm.

EE14. The dressing of any one of EE1-EE13 wherein the channels are conical, elliptic cylindrical, or circular cylindrical shaped.

EE15. The dressing of any one of EE1-EE13 wherein the channels are cylindrical shaped.

First and Second Channels

EE16. The dressing of any one of EE1-EE11, wherein the channels comprise channels of a first channel type and channels a second channel type, wherein the channels of the first channel type are different than the channels of the second channel type with respect to one or more of diameter, shape, and channel angle.

EE17. The dressing of EE16, wherein the channels of the first channel type have a diameter of 25 μm to about 2,500 μm.

EE18. The dressing of EE16, wherein the channels of the first channel type have a diameter of 25 μm to about 1,000 μm EE19. The dressing of EE16, wherein the channels of the first channel type have a diameter of 25 μm to about 300 μm.

EE20. The dressing of EE16, wherein the channels of the first channel type have a diameter of 800 μm to about 1000 μm.

EE21. The dressing of any one of EE16-EE20, wherein there are one to 1,600 channels of the first channel type per $cm^2$ of the surface area of the distal side of the sheet.

EE22. The dressing of any one of EE16-EE20, wherein there are one to 500 channels of the first channel type per $cm^2$ of the surface area of the distal side of the sheet.

EE23. The dressing of any one of EE16-EE20, wherein there are one to 100 channels of the first channel type per $cm^2$ of the surface area of the distal side of the sheet.

EE24. The dressing of any one of EE16-EE20, wherein there are one to 10 channels of the first channel type per $cm^2$ of the surface area of the distal side of the sheet.

EE25. The dressing of any one of EE16-EE20, wherein there are 10 to 1000 channels of the first channel type per $cm^2$ of the surface area of the distal side of the sheet.

EE26. The dressing of any one of EE16-EE20, wherein there are 10 to 100 channels of the first channel type per $cm^2$ of the surface area of the distal side of the sheet.

EE27. The dressing of any one of EE16-EE20 wherein the sum of the surface areas defined by the aperture of the channels of the first type is between 0.01% and 10% of the total surface area defined by the sheet, or in embodiments with a non-perforation zone, the sum of the surface area defined by the aperture of the channels of the first type is between 0.01% and 20% of the total surface area of the channel zone.

EE28. The dressing of any one of EE16-EE20 wherein the sum of the surface areas defined by the aperture of the channels of the first type is between 0.01% and 1.0% of the total surface area defined by the sheet.

EE29. The dressing of any one of EE16-EE20 wherein the sum of the surface areas defined by the aperture of the channels of the first type is between 0.1% and 5% of the total surface area defined by the sheet.

EE30. The dressing of any one of EE16-EE20 wherein the sum of the surface areas defined by the aperture of the channels of the first type is between 0.1% and 1% of the total surface area defined by the sheet.

EE31. The dressing of any one of EE16-EE30 wherein the channels of the second channel type have a diameter of 250 μm to about 10 mm.

EE32. The dressing of any one of EE16-EE30 wherein the channels of the second channel type have a diameter of 250 μm to about 5 mm.

EE33. The dressing of any one of EE16-EE30 wherein the channels of the second channel type have a diameter of 250 μm to about 2.5 mm.

EE34. The dressing of any one of EE16-EE30 wherein the channels of the second channel type have a diameter of 250 μm to about 1 mm.

EE35. The dressing of any one of EE16-EE30 wherein the channels of the second channel type have a diameter of 1000 μm to about 5 mm.

EE36. The dressing of any one of EE16-EE35, wherein there are one to 500 channels of the second channel type per $cm^2$ of the surface area of the distal side of the sheet.

EE37. The dressing of any one of EE16-EE35, wherein there are one to 100 channels of the second channel type per $cm^2$ of the surface area of the distal side of the sheet.

EE38. The dressing of any one of EE16-EE35, wherein there are one to 10 channels of the second channel type per $cm^2$ of the surface area of the distal side of the sheet.

EE39. The dressing of any one of EE16-EE35, wherein there are 10 to 100 channels of the second channel type per $cm^2$ of the surface area of the distal side of the sheet.

EE40. The dressing of any one of EE16-EE39 wherein the sum of the surface areas of the channels of the second type is between 0.01% and 10% of the total surface area defined by the sheet or in embodiments with a non-perforation zone, as defined by the channel zone.

EE41. The dressing of any one of EE16-EE39 wherein sum of the surface areas of the channels of the second type is between 0.1% and 10% of the total surface area defined by the sheet or in embodiments with a non-perforation zone, as defined by the channel zone.

EE42. The dressing of any one of EE16-EE39 wherein sum of the surface areas of the channels of the second type is between 0.01% and 1% of the total surface area defined by the sheet or in embodiments with a non-perforation zone, as defined by the channel zone.

EE43. The dressing of any one of EE16-EE39 wherein sum of the surface areas of the channels of the second type is between 0.1% and 1% of the total surface area defined by the sheet or in embodiments with a non-perforation zone, as defined by the channel zone.

EE44. The dressing of any one of EE16-EE43 wherein the channels of the second type have one or more quadric shapes of conical, elliptic cylindrical, or circular cylindrical Thickness EE45. The dressing of any one of EE1-EE44 wherein the dressing has a thickness of 0.1 to 5 mm.

EE46. The dressing of any one of EE1-EE44 wherein the dressing thickness is 0.1 to 3 mm.

EE47. The dressing of any one of EE1-EE44 wherein the dressing thickness is 0.1 to 2 mm.

EE48. The dressing of any one of EE1-EE44 wherein the dressing thickness is 0.2 to 2 mm.

Sheet Dimensions

EE49. The dressing of any one of EE1-EE48 wherein the sheet width is 4 mm to 50 cm and the sheet length is 10 mm to 20 meters.

EE50. The dressing of any one of EE1-EE48 wherein the sheet width is 20 mm to 30 mm and the sheet length is 20 mm to 20 meters.

EE51. The dressing of any one of EE1-EE48 wherein the sheet width is 30 mm to 300 mm and the sheet length is 30 mm to 20 meters.

EE52. The dressing of any one of EE1-EE48 wherein the sheet width is 60 mm to 300 mm and the sheet length is 60 mm to 20 meters.

Topical Agent

EE53. The dressing of any one of EE1-EE52 further comprising a topical agent wherein the topical agent is adhered to, impregnated in, or affixed to and impregnated in the sheet and/or added periodically to the distal side of the dressing.

EE54. The dressing of EE53 wherein the topical agent is an anti-itch compound and optionally is Sarna, Itch X, Calamine, or any anti-itch compound described herein.

EE55. The dressing of EE53 wherein the topical agent is an anti-inflammatory compound and optionally is hydrocortisone or any anti-inflammatory compound described herein.

EE56. The dressing of EE53 wherein the topical agent is an antifungal compound and optionally an imidazole, triazole, thiazole, allylamine, or echinicandins topical antifungal agents.

EE57. The dressing of EE55 wherein the antifungal agent is one or more imidazole antifungal agent and optionally one or more of a bifonazole, butoconazole, clotrimazole, econazole, fenticonazole, isoconazole, ketoconazole, luliconazole, miconazole, omoconazole, oxiconazole, sertaconazole, sulconazole, and tioconazole antifungal agent.

EE58. The dressing of EE53 wherein the topical agent is an antibiotic agent and optionally Neosporin or polysporin or any antibiotic agent described herein.

EE59. The dressing of EE53 wherein the topical agent is an anticancer topical agent and optionally 5-Flourouracil, NME, or acyclovir or any anticancer agent described herein.

EE60. The dressing of EE53 wherein the topical agent is a biological extract.

EE61. The dressing of any one of EE53 wherein the biological extract is a jatropha extract.

Adhesive

EE62. The dressing of any one of EE1-EE61 wherein the adhesive is 5 nm-2 mm thick.

EE63. The dressing of any one of EE1-EE61 wherein the adhesive is 10 nm-1 mm thick.

EE64. The dressing of any one of EE1-EE63 adhesive is not adhered to the sheet within 5 mm of the center of the sheet measured longitudinally (i.e. measured along the width dimension of the sheet).

EE65. The dressing of any one of EE1-EE64 adhesive is not adhered to the sheet within 5 mm of the center of the sheet measured longitudinally.

EE66. The dressing of any one of EE1-EE65 adhesive is not adhered to the sheet within 10 mm of the center of the sheet measured longitudinally.

EE67. The dressing of any one of EE1-EE66 adhesive is not adhered to the sheet within 20 mm of the center of the sheet measured longitudinally.

EE68. The dressing of any one of EE1-EE67 adhesive is not adhered to the sheet within 50 mm of the center of the sheet measured longitudinally.

EE69. The dressing of any one of EE1-EE68 adhesive is not adhered to the sheet within 100 mm of the center of the sheet measured longitudinally.

Water Permeability

EE70. The dressing of any one of EE1-EE69 wherein the dressing is at least 10% more water permeable than the sheet and adhesive without channels, wherein water permeability is measured as set forth herein.

EE71. The dressing of any one of EE1-EE69 wherein the dressing is at least 25% more water permeable than the sheet and adhesive without channels, wherein water permeability is measured as set forth herein.

EE72. The dressing of any one of EE1-EE69 wherein the dressing is at least 50% more water permeable than the sheet and adhesive without channels, wherein water permeability is measured as set forth herein.

EE73. The dressing of any one of EE1-EE69 wherein the dressing is at least 100% more water permeable than the sheet and adhesive without channels, wherein water permeability is measured as set forth herein.

EE74. The dressing of any one of EE1-EE69 wherein the dressing is at least 200% more water permeable than the sheet and adhesive without channels, wherein water permeability is measured as set forth herein.

EE75. The dressing of any one of EE1-EE69 wherein the dressing is at least 400% more water permeable than the sheet and adhesive without channels, wherein water permeability is measured as set forth herein.

EE76. The dressing of any one of EE1-EE69 wherein the dressing is at least 1000% more water permeable than the sheet and adhesive without channels, wherein water permeability is measured as set forth herein.

Air Permeability

EE77. The dressing of any one of EE1-EE76 wherein the dressing is at least 10% more air permeable than the sheet and adhesive without channels, wherein air permeability is measured as set forth herein.

EE78. The dressing of any one of EE1-EE76 wherein the dressing is at least 25% more air permeable than the sheet and adhesive without channels, wherein air permeability is measured as set forth herein.

EE79. The dressing of any one of EE1-EE76 wherein the dressing is at least 50% more air permeable than the sheet and adhesive without channels, wherein air permeability is measured as set forth herein.

EE80. The dressing of any one of EE1-EE76 wherein the dressing is at least 100% more air permeable than the sheet and adhesive without channels, wherein air permeability is measured as set forth herein.

EE81. The dressing of any one of EE1-EE76 wherein the dressing is at least 200% more air permeable than the sheet and adhesive without channels, wherein air permeability is measured as set forth herein.

EE82. The dressing of any one of EE1-EE76 wherein the dressing is at least 400% more air permeable than the sheet and adhesive without channels, wherein air permeability is measured as set forth herein.

EE83. The dressing of any one of EE1-EE76 wherein the dressing is at least 1000% more air permeable than the sheet and adhesive without channels, wherein air permeability is measured as set forth herein.

Vapor Permeability

EE84. The dressing of any one of EE1-EE83 wherein the dressing is at least 10% more vapor permeable than the sheet and adhesive without channels, wherein vapor permeability is measured as set forth herein.

EE85. The dressing of any one of EE1-EE83 wherein the dressing is at least 25% more vapor permeable than the sheet and adhesive without channels, wherein vapor permeability is measured as set forth herein.

EE86. The dressing of any one of EE1-EE83 wherein the dressing is at least 50% more vapor permeable than the sheet and adhesive without channels, wherein vapor permeability is measured as set forth herein.

EE87. The dressing of any one of EE1-EE83 wherein the dressing is at least 100% more vapor permeable than the sheet and adhesive without channels, wherein vapor permeability is measured as set forth herein.

EE88. The dressing of any one of EE1-EE83 wherein the dressing is at least 200% more vapor permeable than the sheet and adhesive without channels, wherein vapor permeability is measured as set forth herein.

EE89. The dressing of any one of EE1-EE83 wherein the dressing is at least 400% more vapor permeable than the sheet and adhesive without channels, wherein vapor permeability is measured as set forth herein.

EE90. The dressing of any one of EE1-EE83 wherein the dressing is at least 1000% more vapor permeable than the sheet and adhesive without channels, wherein vapor permeability is measured as set forth herein.

Wickability

EE91. The dressing of any one of EE1-EE90 wherein the dressing is at least 10% more wickable than the sheet and adhesive without channels, wherein wickability is measured as set forth herein.

EE92. The dressing of any one of EE1-EE90 wherein the dressing is at least 25% more wickable than the sheet and adhesive without channels, wherein wickability is measured as set forth herein.

EE93. The dressing of any one of EE1-EE90 wherein the dressing is at least 50% more wickable than the sheet and adhesive without channels, wherein wickability is measured as set forth herein.

EE94. The dressing of any one of EE1-EE90 wherein the dressing is at least 100% more wickable than the sheet and adhesive without channels, wherein wickability is measured as set forth herein.

EE95. The dressing of any one of EE1-EE90 wherein the dressing is at least 200% more wickable than the sheet and adhesive without channels, wherein wickability is measured as set forth herein.

EE96. The dressing of any one of EE1-EE90 wherein the dressing is at least 400% more wickable than the sheet and adhesive without channels, wherein wickability is measured as set forth herein.

EE97. The dressing of any one of EE1-EE90 wherein the dressing is at least 1000% more wickable than the sheet and adhesive without channels, wherein wickability is measured as set forth herein.

Protective Layer

EE98. The dressing of any one of EE1-EE97 further comprising a first protective layer releasably secured to the dressing.

EE99. The dressing of EE98, wherein the first protective layer is secured to the proximal side of the sheet.

EE100. The dressing of EE99 further comprising a second protective layer secured to the distal side of the sheet.

Non-Perforation Zone

EE101. The dressing of any one of EE1-EE100 further comprising a non-perforation zone.

EE102. The dressing of EE101 wherein the non-perforation zone is at least 0.25 cm from the periphery measure along the width.

EE103. The dressing of EE102 wherein the non-perforation zone is at least 0.5 cm from the periphery measure along the width.

EE104. The dressing of EE102 wherein the non-perforation zone is at least 0.9 cm from the periphery measure along the width.

EE105. The kit comprising the dressing of any one of EE1-EE104 further comprises a sealed envelope, wherein the sheet is inside the envelope.

EE106. The kit of EE105 wherein the dressing is sterile.

EE107. A kit comprising the dressing of any one of any one of EE1-EE100 further comprising a tape dispenser and a spool wherein the dressing is wrapped around the spool.

EE108. The dressing of any of EEs 1-2, 3.5, 4, 6, or 7 wherein the sheet is nonwoven rayon.

The dressing of EE108 wherein the moisture vapor permeability of the dressing when measured at 37° C. and 100% to 10% relative humidity in the area without channels is a value selected from at least 100 gms/m$^2$/24 hours, at least 500 gms/m$^2$/24 hours, at least 1000 gms/m$^2$/24 hours, at least 2000 gms/m$^2$/24 hours, and between 2,500 and 6,000 gms/m$^2$/24 hours.

The dressing of EE 108 or EE 109 having a tensile strength at break of 5 lbs per inch width (89 Kg/meter width).

The dressing of any one of EEs 108 through 110 wherein the sheet is a thickness of between 0.05 and 0.25 mm.

The dressing of any one of EEs 108 through 111 wherein the dressing is elongatable to 20% to 30%.

EE109. The dressing of any one of EEs 108 through 112 wherein the distal side of the sheet is configured to be exposed to air when in use.

EE110. The dressing of any one of EEs 108 through 113 wherein the width of the dressing is 1 inch to 12 inches.

EE111. The dressing of any one of EEs 108 through 114 wherein the distal side of the sheet is configured to be exposed to air when in use.

EE112. The dressing of any one of EEs 108 through 115 wherein the channels are 0.25 to 1.5 mm in diameter.

EE113. The dressing of any one of EEs 108 through 116 wherein the channels are 5 to 25 per cm$^2$.

EE114. The dressing of any one of EEs 108 through 117 wherein none of the channels are located within 0.25 cm of the periphery measured along the width.

EE115. The dressing of any one of EEs 108 through 118 wherein the sheet further comprises a medicament.

EE116. The dressing of any one of EEs 108 through 119 wherein the sheet further comprises extracts of jatropha, kelp, hemp, or combinations thereof.

EE117. The dressing of any one of EEs 108 through 120 wherein the adhesive is a pressure sensitive tackified acrylate.

EE118. The dressing of any one of EEs 108 through 121 wherein there is two or more channel zones and one or more non-perforation zones of at least 0.5 cm running parallel to the periphery measured along the width of the dressing, located between the channel zones.

EXAMPLES

The following examples are intended to illustrate but not to limit the invention. Moreover, scientific discussions below of underlying mechanisms gleaned from the data are also not meant as limitations of the inventions described here.

Example 1 Manufacturing

Commercially available paper tape was obtained as starting material (i.e. cellulosic sheet and adhesive). Three products were used, namely McKesson MediPak™ Performance Plus Paper Surgical Tape (1"×10 yds), Micropore paper tape plus (3M) McKesson, and McKesson Premium Surgical Tape, Paper, (1"×10 yds).

Next, the cellulosic sheets were removed, in part, from the roll and subjected to macroporation (described below).

Macroporation was performed by rolling a micro-needle dermatalogic roller. A typical dermaroller was used, i.e. a drum-shaped roller studded with 192 fine microneedles in eight rows, 0.5-1.5 mm in length and 0.1 mm in diameter. Optionally, the roller is rolled over the tape 1 or more times; e.g. 2-20 times or 5-10 times.

Example 2 Manufacturing Method 2

An instant dressing is made according to FIG. 1 by the procedure illustrated in FIG. 2. Sheets are passed over the roller wherein tension is set as such that the sheet is not elongated. Elliptical channels can be produced by the same device by increasing the tension to the point of elongation the sheet,

Example 3 Product Manufacturing Report

An instant dressing was manufactured having a non-perforation zone and channels as illustrated in FIG. 3 and FIG. 4

The product was manufactured by a cutting 1 mm diameter holes with a punch.

In these embodiments, the superior properties of the instant dressing is due, in part, to the superior exchange functions of the dressing resulting from the interaction of the porous sheet material (i.e. rayon) and the 1 mm channels.

Variability of the specifications of the first production run of the dressing of FIG. 3:

Tape Roll width=+/−0.025" (0.635 mm)

Roll Length=+/−3" (76.2 mm)

Hole to edge=+/−0./039 (1.00 mm)

Material 3M 1533L (Tan)

Variability of the specifications of the first production run of the dressing of FIG. 4

Tape Roll width=+/−0.025" (0.635 mm)

Roll Lenth=+/−3" (76.2 mm)

Hole to edge=+/−0./032 (0.81 mm)

Material 3M 1533L (Tan)

Figure 5:
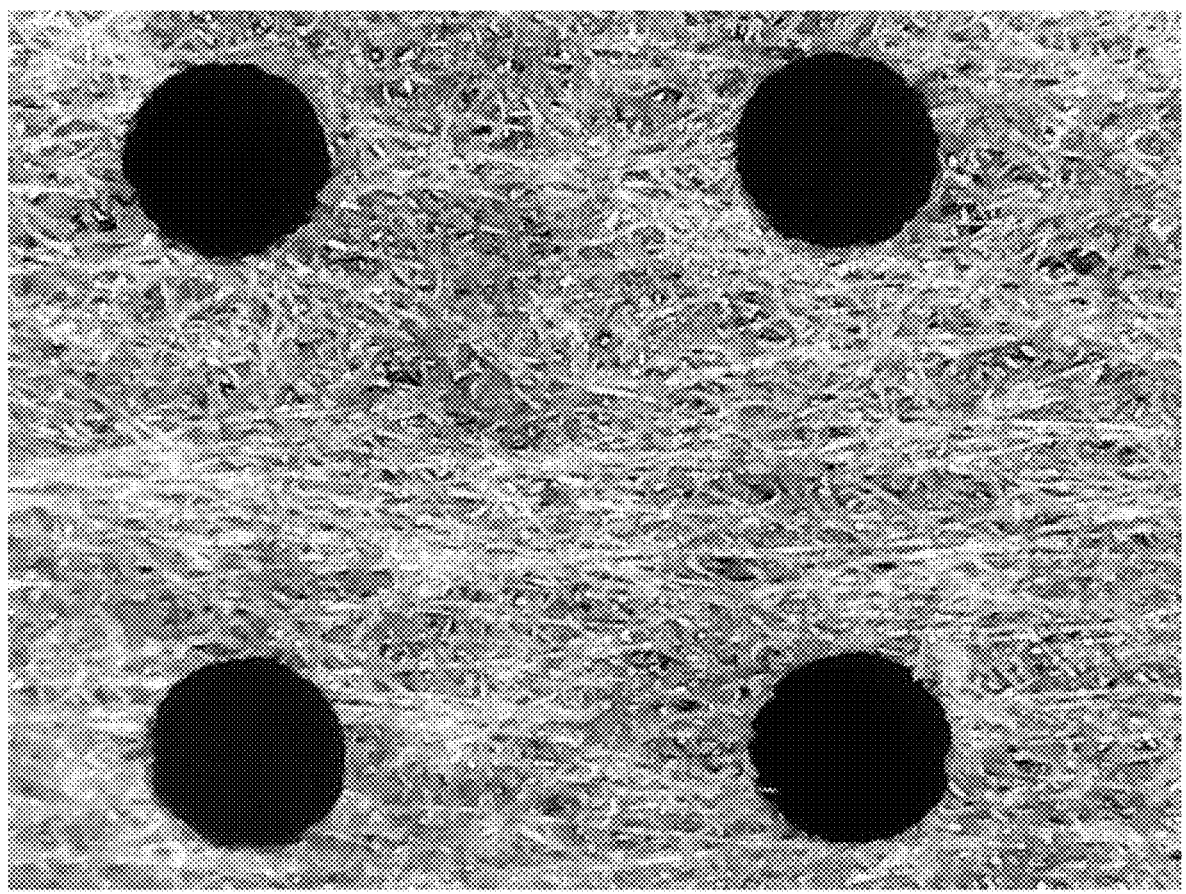
FIG. 5 shows a photomicrograph of one embodiment of the instant invention (of FIG. 3) wherein the channels are 1 mm in diameter.
Figure 6:
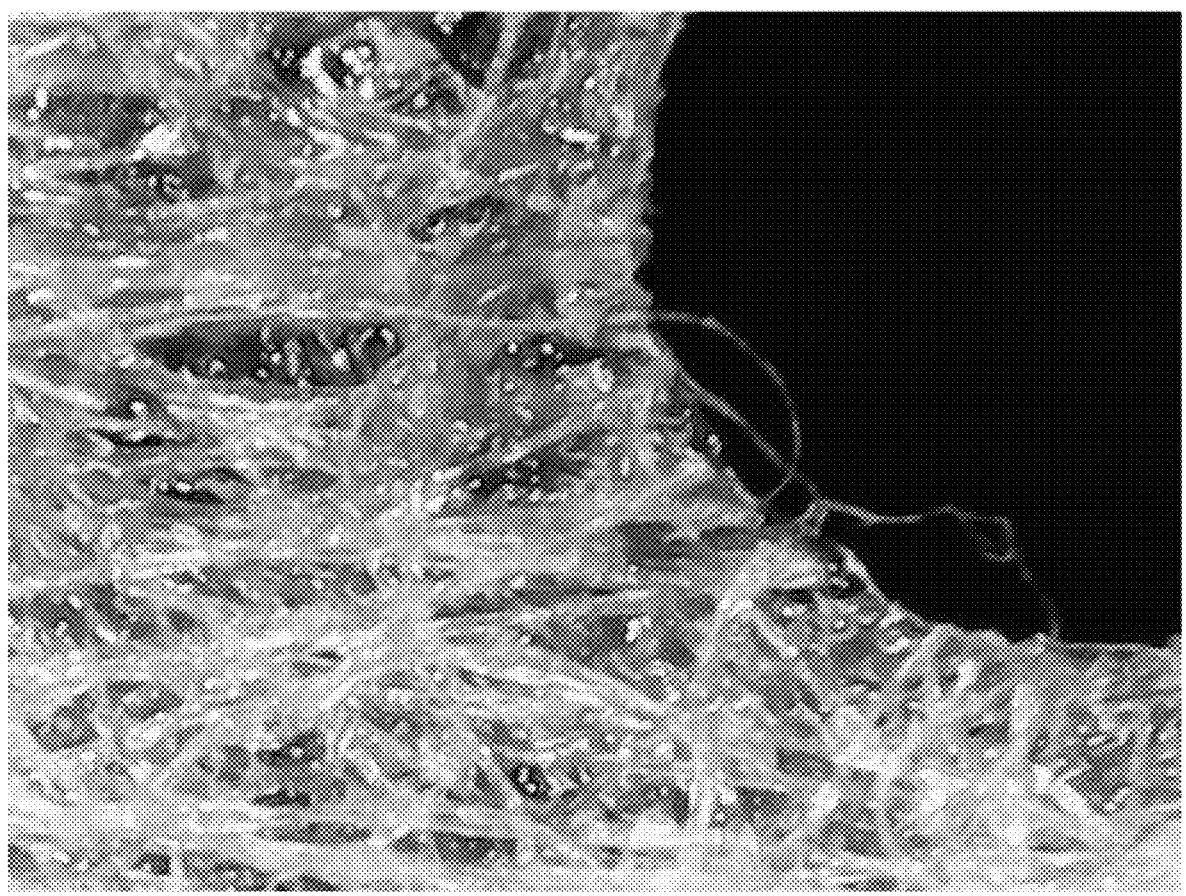
FIG. 6 shows a photomicrograph of one embodiment of the instant invention (of FIG. 3) wherein the channels are 1 mm in diameter.

The instant dressing of was examined microscopically to reveal the porous nature of the sheet material and the 1 mm channels. See FIG. 5 and FIG. 6. Inventor has further observed that, in spite of the fact that much of the surface area of the sheet contains channels (and therefore, no adhesive), the ability of this dressing to adhere to skin is maintained—presumably by the non-perforation zone. Moreover, the enhanced fluid exchange augments the ability to wash the wound and treat the wound with topical agents while providing protection from further abrasion or contamination. Typically, this product can remain adhered to skin for about 2 weeks or more, even when the patient showers, baths, or otherwise washes the wound.

Example 4 Mole Excision or Skin Biopsy

A 40 year old female comes to the medical office with a benign mole to be removed. The surrounding area is cleaned, a local anesthetic is injected, the mole is removed with a scalpel, and the areas is cauterized. A dressing of the instant invention is applied to the wound. The patient is instructed to shower normally after 48 hours and to leave the dressing on until it fell off unassisted. The patient is reexamined after two weeks and reports that the dressing remained on her skin for at least 10 days before falling off.

The wound area shows remarkable healing (e.g. absence of infection or scaring), based on comparison with a large number of patients who are not given any dressing or are given standard paper or cloth surgical tape or a latex adhesive bandage such as Band Aid brand bandage.

This finding is similarly observed with a large number of patients who are similarly treated with the dressing of the instant invention.

Example 5: Case Study 1

Figure 7:
FIG. 7 shows a wound on an 87 year old woman.

An 87 year old woman came into the office for treatment, reporting that she ripped her skin on her right elbow by "brushing it on a counter" four days earlier. See FIG. 7.

The wound (stage 2) was about 3.5 by 7 cm in size. The physician noted that the patient's skin was typical of a woman her age, that is, very thin and fragile.

The physician further noted that this type of wound on the elbow (due to constant motion) is especially difficult to protect with traditional dressings used in the art, have a high risk of infection, and typically take 3 to 4 months to heal.

The wound was cleaned and a dressing of the instant invention was wrapped all the way around the elbow completely covering the wound.

Hydrogen peroxide was applied to the distal side of the dressing with Q-tips to facilitate the movement of blood through the dressing and to provide antisepsis.

The patient was given instructions to shower daily to rinse the tape (and thus the wound), dry and then apply polysporin ointment to top of tape (delivering it to wound). It was not necessary to keep the wound and dressing dry. Different than all other wound dressings which would require daily wound dressing changes (resulting in disruption of the wound and the surrounding skin), the patient did not need to change the dressing at all. Additionally, because of the developmental nature of the dressing of the instant invention, the patient was instructed to wear long sleeves when in public.

Figure 8:
FIG. 8 shows the same area of the skin after 20 days of treatment.

The patient returned 20 days later. At this time, the dressing was beginning to peel off. The dressing was easily removed without discomfort; the physician noted that the dressing "just fell off with gentle unwrapping". The physician noted that this healing was remarkable compared to his observations of other similar wounds of similar aged patients and skin health, whether treated and not bandaged, or treated and bandaged with tradition gauze dressing or any of the various surgical tape known in the art. See FIG. 8.

Example 6. Case Study 2

Figure 9:
FIG. 9 shows a wound on a 64 year old man.

A 64 year old man came in for medical care of tear (stage 2) wound recently received from rubbing his proximal dorsal forearm on his wheelchair. See FIG. 9.

The wound was treated and the patient was instructed, similarly as in Case 1.

Figure 10:
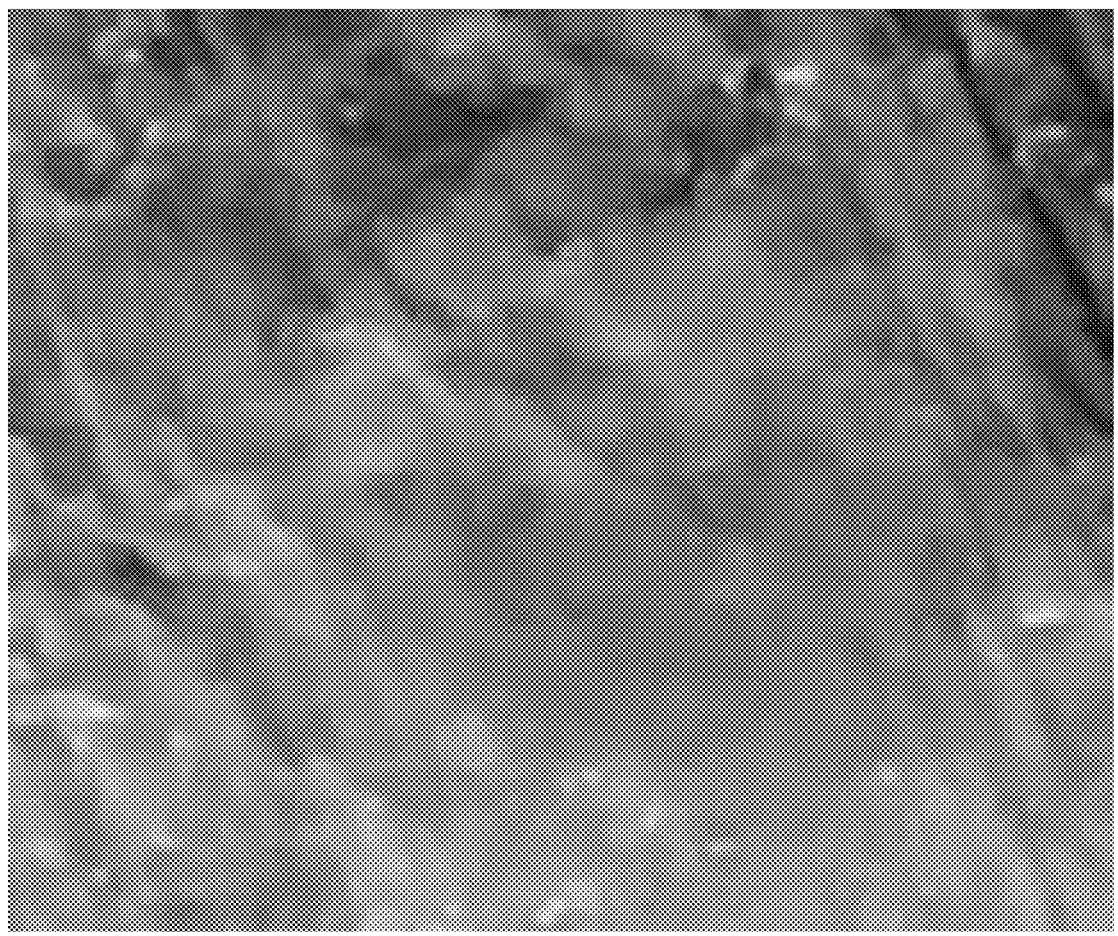
FIG. 10 shows the same area of the skin from FIG. 9 after 10 days of treatment.

The patient returned to the office 10 days later. The dressing was removed with ease. The patient noticed no discomfort or pulling. Remarkably, the physician noted that there was no sign of the wound, edema, or infection. This is in contrast with similar aged patients and skin health, whether treated and not bandaged, or treated and bandaged with tradition gauze dressing or any of the various surgical tape known in the art. See FIG. 10

Example 7 Case Study 3

Figure 11:
FIG. 11 shows a wound on a 40 year old woman.

A 40 year old woman came in for medical care of a distal anterior crural Stage 2+ burn. The wound was recently received from contact with the exhaust of a motorcycle. See FIG. 11.

The wound was treated and the patient was instructed, similarly as in Case 1.

Figure 12:
FIG. 12 shows the same area of the skin from the same women as shown FIG. 11 after 30 days of treatment.

The patient returned to the office 30 days later. The physician observed that the dressing remained attached, yet was easily removed. There was minimal sign of the wound and no sign of edema, infection, or scar tissue. This is in contrast with similar aged patients and skin health, whether treated and not bandaged, or treated and bandaged with tradition gauze dressing or any of the various surgical tape known in the art. See FIG. 12.

Example 8

Applicant has discovered several medical conditions where wide dressings were useful, yet with wider dressings, there is some likelihood of tearing of the dressing. In order to maintain the preferable MVP, stretch, breathability, and other properties taught herein with wider dressings, Applicant has discovered that including a non-perforation zone running parallel to the periphery at the widths located between two channel zones, achieves the strength required by wider dressings. Such a dressing is shown in FIG. 13.

We claim:

1. A dressing comprising a sheet and an adhesive, wherein:
   a. the adhesive is a pressure-sensitive adhesive and is adhered to the sheet,
   b. (i) the sheet comprises sheet material, (ii) the sheet has channels forming a channel zone; (iii) the sheet has a proximal side comprising a surface area, and a distal side comprising a surface area, and (iv) the sheet material demonstrates at least water permeability;
   c. the channels (i) traverse the sheet from the proximal side to the distal side at an angle; (ii) are 1 to 160,000 in number per cm$^2$ of the distal side surface area; and (iii) have a diameter of 25 µm to about 10 mm;
   d. the adhesive, the sheet, and the dressing are dermatologically acceptable;
   e. the channel angle is from 20 degrees to 90 degrees relative to the sheet;
   f. the sheet has a length and a width;
   g. the adhesive is adhered to the proximal side of the sheet;
   h. the sheet material is rayon;
   i. the sheet material without the channels consists of: an air permeability of 0.01 cm$^3$/s/cm$^2$ to 1000 cm$^3$/s/cm$^2$; and a moisture vapor permeability of at least 500 gms/m$^2$/24 hours when measured at 37 degrees C. and 100% to 10% relative humidity; and
   j. the dressing has a plurality of channel zones and a plurality of non-perforation zones of at least 0.5 cm width running parallel to a periphery measured along the width of the dressing wherein at least one of the non-perforation zones is positioned between channel zones of the plurality of channel zones.

2. A method of treating a wound comprising the steps of applying the dressing of claim 1 to skin;
   washing the wound or adding a topical agent to the distal side of the dressing, and
   keeping the wound covered with the dressing for at least 10 days without removing the dressing.

3. The method of claim 2, wherein the dressing is not removed from the skin for at least 10 days.

4. The method of claim 3, wherein the dressing is not removed from the skin for at least 20 days.

5. The method of claim 2, wherein the wound is a pressure sore.

6. The method of claim 5, wherein the dressing has a width of at least 20 cm.

7. The method of claim 2 further comprising providing an adhesive solution and a topical agent wherein the topical agent and the adhesive solution are admixed; and applying the admixture to the skin in an area to come in contact with a periphery of the dressing thereby reducing occurrences of the dressing becoming unattached to a wound area at the periphery.

8. The method of claim 5, wherein the pressure sore is a bed sore or a wheel chair-induced pressure sore.

9. The dressing of claim 1 wherein the sheet material is nonwoven rayon.

10. The dressing of claim 1 wherein the dressing further comprises an extract of one or more of jatropha, kelp, and hemp.

11. The dressing of claim 1 wherein a sum of surface areas defined by apertures of the channels is between 0.01% and 10% of a total surface area defined by the sheet.

12. The dressing of claim 1 wherein the dressing has a tensile strength at break of 5 lbs per inch width (89 kg/meter width), wherein the sheet is a thickness of between 0.05 and 0.25 mm, and wherein the dressing is elongatable in a range of 20% to 30%.

13. The dressing of claim 1, further comprising one or more topical agents, optionally wherein the one or more topical agents are selected from the group consisting of an anti-itch compound, an anti-inflammatory agent, an antibiotic, an anti-fungal agent, an anti-cancer agent, an antiviral agent, a natural marine extract, a natural biologic agent, and a mixture thereof.

14. The dressing of claim 1, wherein other than the sheet, the adhesive, and an optional liner, the dressing comprises no other material layers.

15. The dressing of claim 1, wherein the sheet does not contain an intervening compartment.

16. The dressing of claim 1, wherein the length is longer than the width.

* * * * *